US006346652B1

(12) United States Patent
Schrock et al.

(10) Patent No.: US 6,346,652 B1
(45) Date of Patent: Feb. 12, 2002

(54) ASYMMETRIC RING-CLOSING METATHESIS REACTIONS INVOLVING ACHIRAL AND MESO SUBSTRATES

(75) Inventors: Richard R. Schrock, Winchester; Amir H. Hoveyda, Belmont, both of MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/114,692

(22) Filed: Jul. 13, 1998

(51) Int. Cl.[7] .......................... C07C 6/02; C07D 307/00

(52) U.S. Cl. ..................... 585/643; 585/645; 585/646; 585/940; 549/429; 549/507; 549/1; 549/9; 549/10; 549/13; 549/29; 549/200; 549/214

(58) Field of Search ................................ 585/643, 645, 585/646, 940; 549/429, 507, 1, 9, 10, 13, 29, 200, 214

(56) References Cited

U.S. PATENT DOCUMENTS

| | | | | | |
|---|---|---|---|---|---|
| 3,883,606 | A | * | 5/1975 | Banks | 585/364 |
| 4,654,462 | A | | 3/1987 | Basset et al. | |
| 5,516,953 | A | | 5/1996 | Feldman et al. | |
| 5,519,101 | A | * | 5/1996 | Nubel et al. | 526/142 |
| 5,606,085 | A | * | 2/1997 | Bell et al. | 556/57 |
| 5,639,900 | A | | 6/1997 | Bell et al. | |
| 5,675,051 | A | | 10/1997 | Chauvin et al. | |
| 5,739,396 | A | | 4/1998 | Trost et al. | |
| 5,747,409 | A | | 5/1998 | Commereuc | |
| 5,750,815 | A | | 5/1998 | Grubbs et al. | |
| 5,849,851 | A | * | 12/1998 | Grubbs et al. | 526/93 |
| 5,922,863 | A | * | 7/1999 | Grubbs et al. | 540/538 |
| 5,969,170 | A | * | 10/1999 | Grubbs et al. | 556/21 |

OTHER PUBLICATIONS

K.M. Totland et al., "Ring Opening Metathesis Polymerization with Binaphtholate or Biphenolate Complexes of Molybdenum", Macromolecules, vol. 29, No. 19, pp. 6114–6125, 1996.
R. O'Dell et al., "Polymerization of Enantiomerically Pure 2,3–Dicarboalkoxynorbornadienes and 5,6–Disubstituted Norbornenes by Well–Characterized Molybdenum Ring-Opening Metathesis Polymerization Initiators, Direct Determination of Tacticity in Cis, Highly Tactic and Trans, Highly Tactic Polymers", J.Am.Chem.Soc., vol. 116, No. 8, pp. 3414–3423, 1994.
D. McConville et al., "Synthesis of Chiral Molybdenum ROMP Initiators and All–Cis Highly Tactic Poly(2, 3–(R)$_2$norbornadiene) (R = CF$_3$ or CO$_2$Me)", J.Am.Chem-.Soc., vol. 115, No. 10,pp. 4413–4414, 1993.
O. Fujimura et al., "The Synthesis of Cyclic Enol Ethers via Molybdenum Alkylidene–Catalyzed Ring–Closing Metathesis", J.Org.Chem., vol. 59, No. 15, pp. 4029–4031, 1994.

O. Fujimura and R. H. Grubbs, "Asymmetric Ring–Closing Metathesis Catalyzed by Chiral Molybdenum Alkylidene Complexes", J.Org.Chem., vol. 63, No. 3, pp. 824–832, 1998.
G.C. Fu and R.H. Grubbs, "The Application of Catalytic Ring–Closing Olefin Metathesis to the Synthesis of Unsaturated Oxygen Heterocycles", J.Am.Chem.Soc., vol. 114, pp. 5426–5427, 1992.
G.C. Fu and R.H. Grubbs, "Synthesis of Nitrogen Heterocycles via Catalytic Ring–Closing Metathesis of Dienes", J.Am.Chem.Soc., vol. 114, No. 18, pp. 7324–7325, 1992.
J.A. Heppert et al., "Asymmetric Alkylidene and Oxo Complexes of Tungsten (VI)", Organometallics, vol. 12, No. 7, pp. 2565–2572, 1993.
O. Fujimura and R.H. Grubbs, "Asymmetric Ring–Closing Metathesis: Kinetic Resolution Catalyzed by a Chiral Molybdenum Alkylidene Complex", J.Am.Chem.Soc., vol. 118, No. 10, pp. 2499–2500, 1996.
O. Fujimura et al., "Synthesis of New Chiral Ligands and Their Group VI Metal Alkylidene Complexes", Organometallics, vol. 15, No. 7, pp. 1865–1871, 1996.
M. Schuster and S. Blechert, "Olefin Metathesis in Organic Chemistry", Angew.Chem.Int.Ed.Engl. vol. 36, pp. 2037–2056, 1997.
Z. Xu et al., "Applications of Zr–Catalyzed Carbomagnesation and Mo–Catalyzed Macrocyclic Ring Closing Metathesis in Asymmetric Synthesis, Enantioselective Total Synthesis of Sch 38516 (Fluvirucin B$_1$)", J.Am.Chem.Soc., vol. 119, No. 43, pp. 10302–10316, 1997.
J. Bao et al., "Synthesis, Resolution, and Determination of Absolute Configuration of a Vaulted 2,2'–Binaphthol and a Vaulted 3,3'–Biphenanthrol (VAPOL)", J.Am.Chem.Soc., vol. 118, No. 14, pp. 3392–3405, 1996.

\* cited by examiner

*Primary Examiner*—Walter D. Griffin
(74) *Attorney, Agent, or Firm*—Wolf, Greenfield & Sacks, P.C.

(57) ABSTRACT

A composition and method for the catalytic conversion of a racemic mixture of dienes to a cyclic olefin by a ring-closing metathesis (RCM) reaction are disclosed. The composition, a transition metal complex with an M=C reaction site, contains a bidentate dialkoxide of at least 80% optical purity. Because the M=C reaction site is of a sufficient shape specificity, conferred in part by the dialkoxide of sufficient rigidity and a M=N—R[1] site, reacting the composition with a mixture of two enantiomeric dienes results in an olefin metathesis product that has at least a 50% enantiomeric excess of one enantiomer in the mixture. A method is also provided for reacting a composition with a racemic diene mixture to generate a metathesis product that has an enantiomeric excess of at least 50%. Methods are also provided for catalytic enantioselective desymmetrization. One method involves an olefin metathesis reaction with a molecular substrate having a plane of symmetry to form a product free of a plane of symmetry. Another method provides a desymmetrization reaction to occur in the absence of solvent. A method for producing quaternary carbon centers through a desymmetrization reaction is also described.

70 Claims, 3 Drawing Sheets

ASYMMETRIC RING-CLOSING METATHESIS REACTIONS INVOLVING ACHIRAL AND MESO SUBSTRATES

This invention was made with government support under Grant Number CHE-9700736 awarded by the National Science Foundation. The government has certain rights in the invention.

FIELD OF INVENTION

The present invention relates generally to organometallic catalysts, and more specifically to the catalytic conversion of a racemic mixture of dienes to a cyclic olefin by a ring-closing metathesis (RCM) reaction. The present invention also provides a method for converting achiral or meso substrates into at least one enantiomer of a product through reactions referred to as a catalytic, enantioselective desymmetrization reactions.

BACKGROUND OF THE INVENTION

The formation of carbon—carbon bonds remains among the most important reactions in synthetic organic chemistry. Consequently, the development of transition metal catalyzed carbon—carbon bond formation represented a significant advance in organic synthesis. One reaction involving transition metal catalyzed carbon—carbon formation is olefin metathesis. Olefin metathesis can be defined conceptually as a mutual exchange of alkylidene units between two olefins involving both the formation and cleavage of carbon—carbon double bonds. Transition metal ion catalysts allow this reaction to proceed in a facile manner through a [2+2] cycloaddition between an M=C center and a carbon—carbon double bond. When two olefin groups are located on the same molecule and are subjected to olefin metathesis conditions, a ring-closing metathesis (RCM) reaction can occur in which a series of olefin metathesis reactions produce a cyclic olefin. Ring-closing metathesis is most facile for 5–7 membered ring systems because of the low ring strain afforded by these compounds. Ruthenium and molybdenum alkylidene complexes have proven capable of ring closing dienes having a variety of functional groups.

RCM reactions are generally plagued by undesirable reactions that compete with ring formation, such as acyclic diene metathesis and ring opening metathesis. The former reaction involves polymer formation through the metathesis of terminal dienes whereas the latter reaction comprises metathesis reactions of the ring-closed cyclic olefin. These competing reactions can be circumvented, for example, by performing the reactions under dilute conditions, optimizing ring sizes and utilizing hindered olefin substrates. The latter strategy is also useful for directing the initial reaction of the metal alkylidene towards one olefinic site in a diene over the other olefinic group.

The development of asymmetric ring closing metathesis has considerable potential as a powerful synthetic tool for the preparation of ring structures of defined stereosymmetry. For example, a logical application of asymmetric RCM is the synthesis of natural products which contain varying sizes of ring systems having pendant functional groups of specific stereosymmetry. U.S. Pat. No. 5,516,953 discloses a process for the preparation of optically active cycloolefins catalyzed by molybdenum and tungsten complexes. This process requires that substrate be initially isolated as an optically active diene. Olefin metathesis is catalyzed by molybdenum and tungsten halide or oxide complexes that may also contain alkoxide or amido ligands. In some instances, a tin, lead, aluminum, magnesium or zinc complex cocatalyst may be required.

U.S. Pat. No. 4,654,462 describes a process for olefin metathesis by a tungsten complex containing two phenoxy groups, a halogen atom, an alkyl radical and a carbene. Stereoselectivity is reported sufficient to control cis/trans isomerization in the metathesis of pure cis or trans olefins.

Only recently, the first report of an asymmetric RCM reaction involving the interaction of a chiral catalyst with a racemic substrate mixture was reported by Grubbs et al. *J. Am. Chem. Soc.* 1996, 118, 2499, *Organometallics* 1996, 15, 1865. A racemic diene substrate was added to a molybdenum alkylidene amido catalyst containing a dialkoxide ligand. At various conversion levels of the starting mixture, the enantiomeric excess of the unreacted diene mixture was analyzed, resulting in enantiomeric excess values of up to 48%. The enantiomeric excess of the ring-closed product was not reported. It was proposed that the dialkoxide had a rigid structure suitable to promote the transfer of asymmetry.

There remains a fundamental need for the synthesis of optically pure products by using asymmetric ring-closing metathesis reactions. In a recent review article, Blechert et al. discuss the state of the art relating to asymmetric RCM reactions, maintaining that "In light of the e.e. [enantiomeric excess] values obtained to date, synthetic applications of this process are currently not envisioned." *Angew. Chem., Int. Ed. Engl.* 1997, 36, 2036. Asymmetric processes only begin to show promise industrially when achieving enantiomeric excess values of at least 80%.

Another class of reactions that further advances the field of asymmetric synthesis is enantioselective desymmetrization reactions. The desymmetrization process involves converting achiral or meso substrates, i.e. substrates having a plane of symmetry, into a molecule having a stereocenter. If the desymmetrization reaction can be carried out enantioselectively, then one enantiomer is produced selectively in high enantiomeric excesses. In particular, desymmetrization reactions involving carbon-carbon bond formation have great potential in the pharmaceutical industry and in natural products synthesis, and only a limited number of examples have been reported in the literature. In Trost et al., palladium-catalyzed cyclization reactions yield chiral products having enantiomeric excesses of no more than 90%. Higher enantiomeric excess values can be obtained but only in the presence of added triethylamine. *J. Org. Chem.* 1998, 63, 1339–1341. In Mikami et al., carbon—carbon bond formation is effected between two substrates in an enantioselective fashion in the presence of a chiral titanium complex. *J. Am. Chem. Soc.* 1992, 114, 6566–6568. The field of asymmetric synthesis, however, remains wide open to increase the variety of desymmetrization reaction types and to improve synthetic conditions such as lower catalyst loadings, increased yields and conversions and decreased reaction times.

It remains a challenge to design a metal catalyst that can catalytically generate compounds having stereocenters while achieving high enantioselectivity.

SUMMARY OF THE INVENTION

In one illustrative embodiment of the present invention, a composition is provided having the structure:

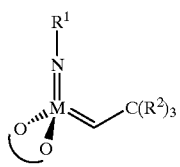

The composition has a chiral dialkoxide ligand, denoted by

wherein the dialkoxide is of at least 80% optical purity.

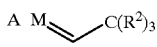

A reaction site is of sufficient shape specificity, defined in part by the dialkoxide of sufficient rigidity and a M=N—R$^1$ site to cause a mixture of two enantiomeric olefins to react with an M=C center of the

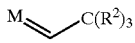

reaction site at different rates. The reaction is an olefin metathesis reaction and the product has at least a 50% enantiomeric excess of one enantiomer present in the original mixture. M is a metal ion, preferably molybdenum or tungsten.

In one embodiment of the invention, the group of atoms defining the shortest chemical bond pathway linking the oxygen atoms in

contains at least four atoms. In another illustrative embodiment of the present invention,

comprises the structure:

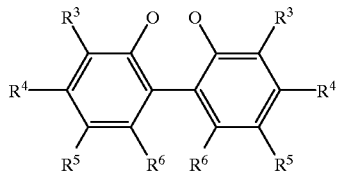

II

The chiral dialkoxide transfers asymmetry to the composition such that the composition is at least 80% optically pure.

In another embodiment of the present invention, a method is provided wherein a diene mixture of enantiomers is reacted with the M=C center of the above-mentioned composition. The method involves allowing a first enantiomer of the mixture to metathesize at M to an extent greater than a second enantiomer to form a product that has an enantiomeric excess of at least 50%. The metathesizing step occurs catalytically.

One aspect of the invention provides a method which includes a step of adding the racemic diene mixture to produce a ring-closed metathesis compound having an enantiomeric excess of at least 50% at 50% conversion of the diene mixture. Moreover, the enantiomeric excess of an enantiomer in the unreacted diene mixture is at least 50% at 50% conversion. The method allows 50% conversion of the racemic diene mixture to be achieved within a time of at least 5 minutes.

In another illustrative embodiment of the present invention, the diene comprises the structure:

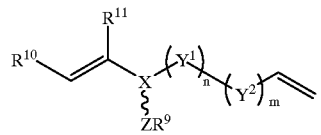

III

The diene contains one unsubstituted olefin group and one hindered olefin group to direct the initial metathesis towards the unsubstituted end. Reaction of the diene with the composition results in the formation of a ring-closed compound. The diene has a stereocenter and is available as a racemic mixture.

Another aspect of the invention provides a method for desymmetrization. The method involves the step of providing a molecular substrate having a plane of symmetry. A desymmetrization reaction is allowed to occur to form a product free of a plane of symmetry. In another aspect, the desymmetrization is allowed to occur in the absence of solvent.

Another aspect of the invention provides a method for catalytic desymmetrization. The method involves the step of providing a molecular substrate having a plane of symmetry and a catalyst. A desymmetrization reaction is allowed to occur to form a product having a quaternary carbon center in at least about 20% enantiomeric excess.

Another aspect of the invention provides a composition comprising a structure:

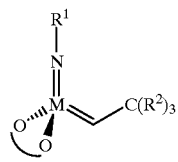

M is a metal ion and

is a chiral dialkoxide of at least 80% optical purity. The dialkoxide has sufficient rigidity such that a

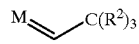

reaction site is of sufficient shape specificity, defined in part by the dialkoxide and a M=N—R site, to cause a molecular substrate having a plane of symmetry to react with a M=C center at the

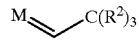

reaction site. A catalytic olefin metathesis product is formed that has at least a 50% enantiomeric excess of at least one enantiomer present in the mixture. The product is free of a plane of symmetry.

Other advantages, novel features, and objects of the invention will become apparent from the following detailed description of the invention when considered in conjunction with the accompanying drawings, which are schematic and which are not intended to be drawn to scale. In the figures, each identical or nearly identical component that is illustrated in various figures is represented by a single numeral. For purposes of clarity, not every component is labeled in every figure, nor is every component of each embodiment of the invention shown where illustration is not necessary to allow those of ordinary skill in the art to understand the invention.

DETAILED DESCRIPTION

Figure 1:
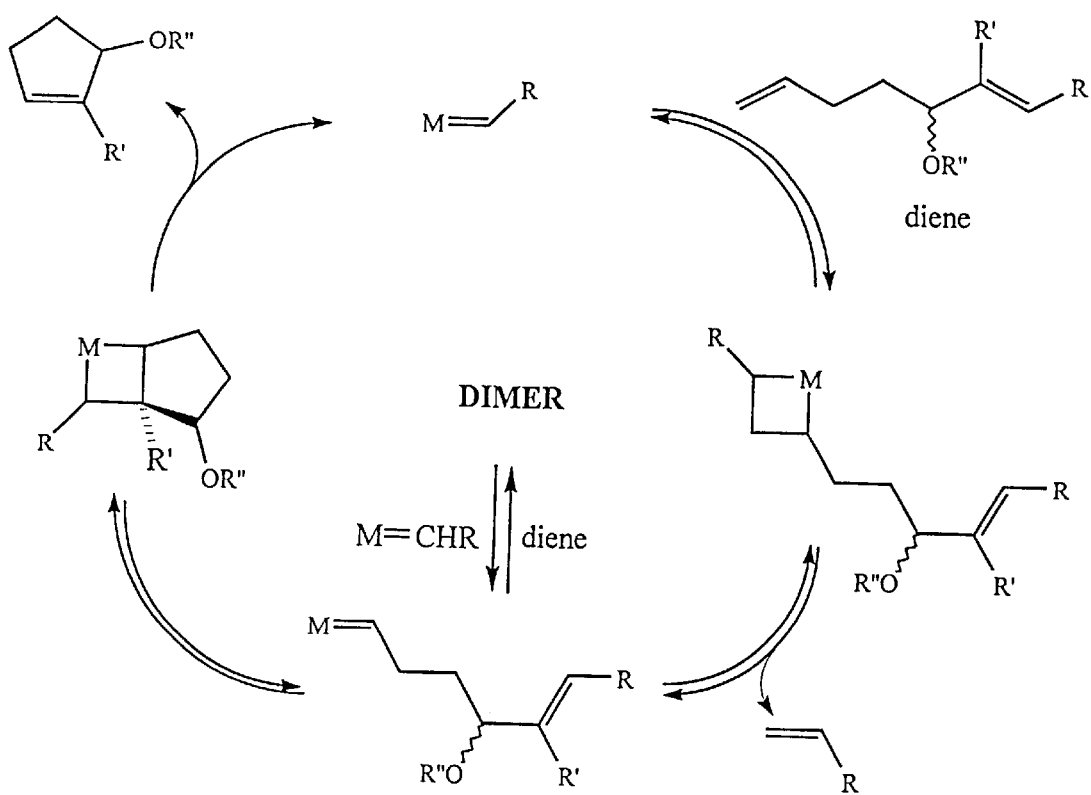
FIG. 1 depicts a proposed mechanism for a ring-closing metathesis catalytic cycle, illustrating the reaction intermediates.

The present invention provides, in one aspect, an olefin metathesis catalyst. In one illustrative embodiment of this aspect of the present invention, a composition is provided comprising the structure:

I

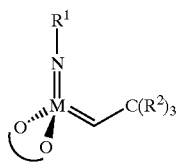

The metal ion, M, is preferably molybdenum or tungsten. The composition has a chiral dialkoxide, denoted by

The term "chiral" herein refers to a molecule that is not superimposable with its mirror image. The resulting nonsu-perimposable mirror images are known as "enantiomers" and are labeled as either an (R) enantiomer or an (S) enantiomer. Because enantiomers contain chiral centers, they are included in a specific type of isomerism called "stereoisomerism." A molecule such as $CX_2WY$ would not have enantiomers; the replacement of one X by another group Z, however, would lead to one enantiomer; conversely the replacement of the other X by Z would lead to the other enantiomer. From this viewpoint, the X atoms in $CX_2WY$ are not equivalent and are defined as "enantiotopic". A "prochiral molecule" is a molecule such as $CX_2WY$ that contains two enantiotopic atoms or groups, such as the X atoms in $CX_2WY$. "Chiral molecules" as used herein also includes by definition prochiral molecules.

$R^1$ and $R^2$ can be the same or different, and each is selected from the group consisting of $C_1$–$C_{12}$ alkyl, heteroalkyl, aryl, heteroaryl and adamantyl. Preferably, $R^1$ is 2,6-dimethylphenyl, 2,6-diethylphenyl or 2,6-diisopropylphenyl and $R^2$ is methyl, ethyl or phenyl.

An "alkoxide" ligand herein refers to a ligand prepared from an alcohol, in that removing the hydroxyl proton from an alcohol results in a negatively charged alkoxide. The alkoxide of the present invention is a linked, bidentate dialkoxide ligand. Moreover, the dialkoxide is chiral and can exist as one of two enantiomers. Each dialkoxide enantiomer interacts with plane-polarized light differently, in that this plane is rotated by both enantiomers to the same extent but in opposite directions. If a sample contains only one enantiomer, a measurement of the sample's optical activity would reveal an "optically pure" compound. The chiral dialkoxide of the present invention is of at least 80% optical purity in that the dialkoxide sample contains 90% of one enantiomer and 10% of the other. The dialkoxide preferably is at least 90% optically pure, more preferably at least 95% optically pure, and more preferably still at least 99% optically pure.

It is a feature of the present invention that a catalytic composition is provided having a dialkoxide of sufficient rigidity such that, in conjunction with an M=N—$R^1$ site, the combination of the dialkoxide and the M=N—$R^1$ site in part confers a shape specificity to a

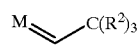

reaction site where the composition reacts with an olefin. This shape specificity, imparted by rigidity of the dialkoxide ligand, is sufficient to allow a mixture of two enantiomeric olefins to react with a M=C center of the

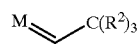

reaction site at different rates. That is, the invention provides a catalyst designed to have shape specificity sufficient to differentiate between enantiomers of a reactant by sterically interacting with one enantiomer almost exclusively or exclusively. A means to achieve a preference for one enantiomer over the other, or enantiomeric selectivity, is kinetic resolution. Enantiomeric selectivity by kinetic resolution involves reducing the steric interactions in the transition state of the reaction of the substrate at the catalyst such that the transition state involving one enantiomer is of lower energy than the transition state of the other enantiomer. Consequently, the term shape specificity in the present invention refers to the shape of an M=C reaction site in the transition state, as formed by the surrounding ligands, such that upon reaction of the substrate with the metal compound, one enantiomer "fits into" the binding site with less steric interaction than the other enantiomer. The transition state energy is lower for the enantiomer with a better "fit" or shape specificity over the other.

In another embodiment, the chiral dialkoxide of at least 80% optical purity has sufficient rigidity such that a

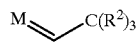

reaction site is of sufficient shape specificity, defined in part by the dialkoxide and a M=N—R site, to cause a molecular substrate having a plane of symmetry to react with a M=C center at the

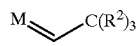

reaction site forming a catalytic olefin metathesis product that is free of a plane of symmetry. The product has at least a 50% enantiomeric excess of at least one enantiomer present in the mixture.

A method to screen for dialkoxides having sufficient rigidity for shape specificity purposes involves obtaining an enantiomeric mixture of a test dialkoxide, isolating one enantiomer and measuring a specific rotation. A dialkoxide of sufficient rigidity would provide a specific rotation as opposed to reverting back to an enantiomeric mixture.

Generally, two enantiomeric olefins can react with an M=C center catalytically to form an olefin metathesis product. Olefin metathesis is defined conceptually as a mutual exchange of alkylidene units between two olefins, as illustrated in eq 1:

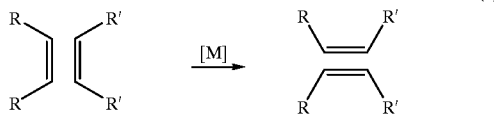

(1)

Although "olefin metathesis" generally refers to a reaction between two olefin or alkene groups, "olefin metathesis" is also used herein to refer to reactions involving at least one alkyne group. Thus, olefin metathesis reactions can occur between two triple bonded groups or between a double bonded and a triple bonded group.

Olefin metathesis can be catalyzed by a metal complex, denoted in the equation as [M]. In the present invention, the metal complex is a chiral metal complex including a chiral metal center that can transform olefin substrates (reactants) into optically pure products. Typically, the substrate is a racemic mixture, the term "racemic" referring to a mixture containing an equal ratio of (R) and (S) enantiomers. The chiral metal complex of the invention can function as an asymmetric catalyst and simplifies the reaction process due to its ability to resolve a racemic mixture in generating a product of high enantioselectivity, or optical purity. The extent of optical purity of a product is gauged by the "enantiomeric excess" or "e.e." of the product mixture. The enantiomeric excess is the difference between the percent of the majority enantiomer minus the percent of the minority isomer, as represented by the equation $[([R]-[S])/([R]+[S])] \times 100$ in which [R] and [S] refers to concentration of the (R) and (S) enantiomer respectively. For example, if a mixture contains a 50% e.e. of the (R) configuration, the mixture contains 75% of the (R) configuration and 25% of the (S) configuration. In the present invention, the a mixture of the two enantiomeric olefins react with the M=C center at different rates to generate an olefin metathesis product that has at least a 50% enantiomeric excess of one enantiomer present in the mixture, preferably at least 85%, more preferably at least 90% and more preferably still at least 95%.

In one embodiment of the invention, a species as defined above is provided including a dialkoxide comprising two linked oxygen atoms such that the group of atoms defining the shortest chemical bond pathway between the two oxygen atoms has at least four atoms. For example, the four atoms can be four unsaturated atoms which confer rigidity to an organic group because they possess less degrees of freedom than a saturated atom. Examples of unsaturated carbon atoms are found in alkene, alkyne or aryl substituents.

The present invention also provides a dialkoxide, which can comprise

comprising the structure:

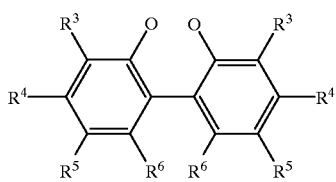

II wherein $R^3$–$R^6$ can be the same or different, and each is selected from the group consisting of hydrogen, alkyl, alkenyl, alkynyl, cycloalkyl, cycloalkenyl, cycloalkynyl, aryl, alkaryl, aralkyl and optionally interrupted or terminated by N, O, P, S, heteroalkyl, heteroaryl, carbonyl, acyl, acyloxy, —CHO, —COOR$^7$, —CO$_2$C(R$^7$)$_3$, —CONC(R$^7$)$_2$, cyano, NO$_2$, alkyloxy, aryloxy, hydroxy, hydroxyalkyl, amino, alkylamino, dialkylamino, arylamino, diarylamino, —NR$^7$COR$^8$, thioalkyl, thioaryl, —SO$_2$R$^7$, —SOR$^7$, —SO$_2$OR$^7$, F, Cl, Br, I; R$^7$ and R$^8$ can be the same or different, and each is selected from the group consisting of hydrogen, C$_1$–C$_{12}$ alkyl, C$_1$–C$_{12}$ heteroalkyl, aryl, heteroaryl, hydroxyl, F, Cl, Br and I; and any two R groups where possible can combine to form a closed ring system selected from the group consisting of aryl, heteroaryl, substituted aryl, biaryls, and substituted biaryls. Preferably, $R^3$–$R^6$ can be the same or different and each is selected from the group consisting of C$_1$–C$_{12}$ alkyl, heteroalkyl, aryl, heteroaryl, optionally interrupted or terminated by N or O, and any two R groups where possible can combine to form a closed ring system selected from the group consisting of aryl, heteroaryl, substituted aryl, biaryls and substituted biaryls. More preferably, R$^3$ is i-propyl, t-butyl, cyclohexyl, t-octyl, R$^4$ is hydrogen or C$_1$–C$_2$ alkyl, R$^5$ is hydrogen or C$_1$–C$_2$ alkyl, and R$^6$ is methyl.

The chirality of the dialkoxide according to this embodiment results from steric interactions of the R$^6$ groups maintaining a rotational orientation of the phenyl groups about the biaryl bond such that the two phenyl groups are non-planar with respect to each other. In this manner, the dialkoxide of this embodiment confers chirality to a metal complex, as illustrated below:

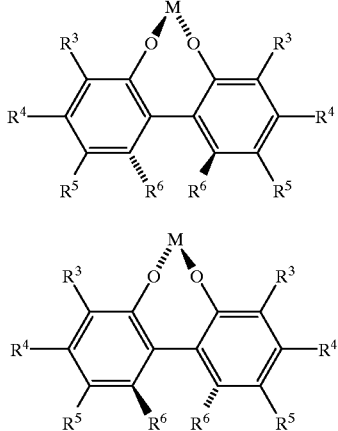

IV

V

In a particularly preferred embodiment, the dialkoxide of the invention confers chirality to the metal complexes IV and V through the interaction between $R^6$ methyl groups of dialkoxide II. The present invention provides a composition that is a chiral metal complex in which the composition is at least 80% optically pure, preferably at least 90% optically pure, more preferably at least 95% optically pure, and more preferably still at least 99% optically pure.

While not wishing to be bound by any theory, specificity of the catalyst of the invention where the alkoxide is II is due to the following: Upon binding the dialkoxide to a metal center, a seven-membered metallacycle results. This configuration allows bulky functional groups in the $R^3$ positions to point towards the general direction of the M=C reaction center, aiding in providing shape specificity to the M=C reaction site.

In another embodiment of the present invention, the olefin metathesis reaction is a ring-closing metathesis (RCM) reaction in which a ring-closed compound is produced. Preferably, the ring-closed compound is a cyclic olefin. To obtain the cyclic product, the substrate must be a diene to achieve ring-closing through two subsequent olefin metathesis reactions. The diene source of the present invention is a racemic diene mixture where the diene is of from about 4 to about 18 carbons in length, preferably from about 7 to about 12 carbons in length. The double bonds of the diene are separated by enough distance that a ring can be formed. Other considerations for diene selection are described below. Exposing the composition of the present invention to the racemic diene mixture produces a ring-closed compound with high enantioselectivity. This high enantioselectivity is demonstrated at 50% conversion of the racemic diene mixture, in which the ring-closed compound has an enantiomeric excess of at least 50%, preferably at least 85%, more preferably at least 90% and more preferably still at least 95%. The enantiomeric excess of the remaining unreacted diene can also be measured. At 50% conversion of the racemic diene mixture, the unreacted diene has an enantiomeric excess of at least 50%, more preferably at least 85%.

Another aspect of the invention provides a method comprising reacting the composition, I, of the present invention with a diene. In one embodiment of this aspect of the invention, the method comprises reacting an enantiomeric diene mixture with the composition of the present invention and allowing a first enantiomer of the mixture to metathesize at the metal ion, M, to an extent greater than a second enantiomer of the mixture. The resulting product has an enantiomeric excess of at least 50%. The composition is at least 80% optically pure, preferably at least 90% optically pure, more preferably at least 95% optically pure and more preferably still 99% optically pure. Preferably, the metal ion is molybdenum or tungsten.

In another embodiment of the invention, addition of the diene mixture to the compound produces a ring-closed compound. Preferably the ring-closing reaction is a ring-closing metathesis reaction. In this embodiment the enantiomeric diene mixture of the present invention comprises the structure:

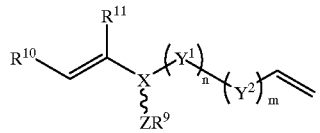

III

The method of reacting the diene with the composition can optionally include the step of dissolving the composition in a solvent before adding the diene.

The extent of substitution on the respective diene olefinic groups can be important in preventing undesirable side reactions which would decrease metathesis activity and product selectivity. Due to steric demands, an unsubstituted olefin reacts with an M=C bond at a faster rate than a substituted olefin. A diene containing two terminal unsubstituted olefin groups, however, will react with M=C reaction sites to generate polymers by the well-known acyclic diene metathesis reaction. If desirable, the rate of metathesis can be decreased to the extent that polymer formation is negligible typically by substituting the hydrogen atoms on the second olefin group with bulkier substituents such as methyl, ethyl, or the like, for example the $R^{10}$ or $R^{11}$ groups in the above-mentioned structure.

Referring to FIG. 1, a proposed mechanism for an RCM catalytic cycle involving diene III is shown, illustrating the reasons for the preferred diene structure according to this embodiment. At the top of FIG. 1, a complex containing a M=C reaction site reacts with a diene structure of the present invention at the unsubstituted terminal olefin site. A metallacyclobutane intermediate results that subsequently releases an olefin and a metal complex containing the reacted diene group. This complex can either react with the substituted olefin intramolecularly or with another diene intermolecularly at its unsubstituted terminal olefin site. The latter reaction is unproductive, however, in that the resulting product dimer is unstable and upon reaction with a M=C reaction site, reverts back to the M=C complex. The intramolecular reaction produces a bicyclic compound comprising a metallacyclobutane fused to another closed-ring structure which consequently transforms into cyclic olefin product and a complex containing a M=C reaction site. Yet another undesirable side reaction is metathesis of the cyclic olefin product with the M=C reaction site through a ring-opening metathesis process. Again, designing the diene to produce a cyclic olefin that affords minimal ring strain or that contains a relatively hindered olefin may contribute to a decrease in rate of the ring-opening reaction.

In embodiments of the present invention in which the diene is III, X is selected from the group consisting of $CR^{12}$, N or P. $Y^1$, $Y^2$ and Z can be the same or different and each is selected from the group consisting of $CR^{12}R^{13}$, $NR^{12}$, O or S. When a diene contains main group elements at the X, $Y^1$ or $Y^2$ sites, heterocyclic products can be formed. $R^{10}$ and $R^{11}$ can be the same or different, and each is selected from the group consisting of hydrogen, alkyl, alkenyl, alkynyl, cycloalkyl, cycloalkenyl, cycloalkynyl, aryl, alkaryl, aralkyl and optionally interrupted or terminated by N, O, P, S, heteroalkyl, heteroaryl, carbonyl, acyl, acyloxy, —CHO, —$COOR^{12}$, —$CO_2C(R^{12})_3$, —$CONC(R^{12})_2$, cyano, $NO_2$, alkyloxy, aryloxy, hydroxy, hydroxyalkyl, amino, alkylamino, dialkylamino, arylamino, diarylamino, —$NR^{12}COR^{13}$, thioalkyl, thioaryl, —$SO_2R^{12}$, —$SOR^{12}$, —$SO_2OR^{12}$, F, Cl, Br, I. $R^9$, $R^{12}$ and $R^{13}$ can be the same or different, and each is selected from the group consisting of hydrogen, $C_1$–$C_{12}$ alkyl, $C_1$–$C_{12}$ heteroalkyl, aryl, heteroaryl, hydroxyl, alkylsilyl, arylsilyl, alkarylsilyl, F, Cl, Br and I. Any two R groups, where possible, can combine to form a closed ring system selected from the group consisting of aryl, heteroaryl, substituted aryl, biaryls, and substituted biaryls. The value "n+m" is at least 2. Preferably, n+m ranges from 2 to 4. More preferably, n+m =2. Where n+m=2, the cyclic product is a five-membered ring. Increasing n or m provides for the possibility of forming larger ring systems. Preferably, $Y^1$, $Y^2$ and Z can be the same or different and each is selected from the group consisting of $CR^{12}R^{13}$, $NR^{12}$, O or S. $R^{10}$, $R^{11}$, $R^{12}$, and $R^{13}$ can be the same or different and each is selected from the group consisting of $C_1$–$C_{12}$ alkyl, heteroalkyl, aryl or substituted aryl and $R^9$ is selected from the group consisting $C_1$–$C_{12}$ alkyl, heteroalkyl, aryl or substituted aryl, alkylsilyl, arylsilyl, and alkylarylsilyl. More preferably, X is CH, $Y^1$ and $Y^2$ each are $CH_2$, and $ZR^9$ is selected from the group consisting of acetate, t-butylacetate, trifluoroacetate, and trialkylsilyloxide.

In another embodiment of the invention, a method is provided that generates a ring-closed metathesis compound from a racemic diene mixture such that at 50% conversion of the racemic diene mixture, the product has an enantiomeric excess of at least 50%, preferably 85%, more preferably at least 90% and more preferably still at least 95%. The optical purity of the unreacted diene can also be analyzed and at 50% conversion of the racemic diene mixture, the enantiomeric excess of the unreacted diene is at least 50%, preferably at least 85%. In another embodiment of the invention, a step of adding the diene mixture to the composition results in 50% conversion of the racemic diene mixture within a time of at least 5 minutes.

The present invention also provides a method to achieve enantiomeric selectivity through kinetic resolution. As discussed previously, kinetic resolution can be achieved when a transition state involving the reaction of the M=C center with one enantiomer is of lower energy than a transition state involving the other enantiomer. This lowered transition state energy arises from the shape specificity of the binding site for that one particular enantiomer, the end result being that the one enantiomer undergoes RCM at a faster rate than the other enantiomer. The reaction rate is dependent on the rate constant, in which the rate constant of a reaction involving the (S) enantiomer is labeled as $k_s$, and the rate constant of a reaction involving the (R) enantiomer is denoted by $k_r$, in equations 2 and 3, respectively. For example, to obtain a product mixture containing predominantly the (R) enantiomer, $k_r$ should be sufficiently greater than $k_s$. The present invention provides sufficient kinetic resolution to obtain, for example, the (R) enantiomer of the product such that adequate optical purity, as defined above, is achieved when the value of $S=k_r/k_s$ (eq 4) is at least 10, preferably at least 25.

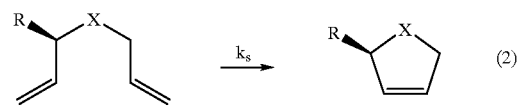

(2)

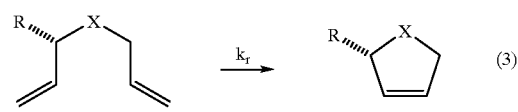

(3)

Relative Rate = $S = k_r/k_s$ (4)

Another aspect of the invention provides a method for catalytic, enantioselective desymmetrization. Desymmetrization reactions involve the transformation of a molecular substrate, i.e. reactant, having a plane of symmetry into a product free of a plane of symmetry where the transformation involves two reactive sites situated on the substrate. For example, the desymmetrization reaction can be carbon-carbon bond forming reaction such as olefin metathesis involving at least two reactive sites. Where only one substrate is involved in the desymmetrization reaction, the olefin metathesis may be a ring-closing metathesis and/or a ring-opening metathesis reaction. In another embodiment, two molecular substrates may be involved in the desymmetrization, such as in a cross-metathesis reaction between a first molecular substrate and a second molecular substrate.

By removing the plane of symmetry in the substrate i.e. a substrate free of a plane of symmetry, preferably the product possesses a stereocenter. Thus in asymmetric synthesis, an advantage of enantioselective desymmetrization over kinetic resolution is the ability to produce optically active products in high yields of up to 100%. Where a product can only be made from a substrate comprising a racemic mixture of enantiomers that are not easily isolated or kinetically resolved, enantioselective desymmetrization may eliminate the need for purification or kinetic resolution. The distinction between kinetic resolution and enantioselective desymmetrization can be illustrated by the examples shown in equations 5 and 6:

(5)

Catalytic Kinetic Resolution

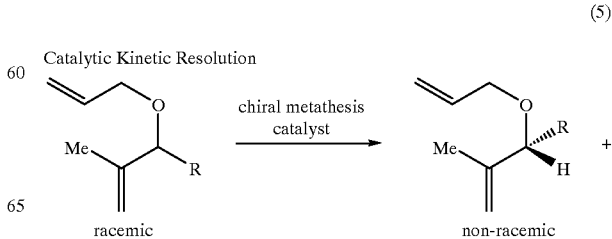

racemic                non-racemic

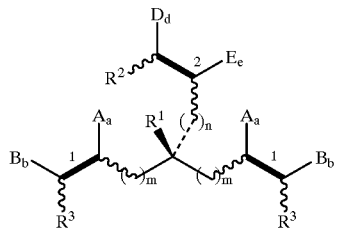

(6)

Catalytic Enantioselective Desymmetrization

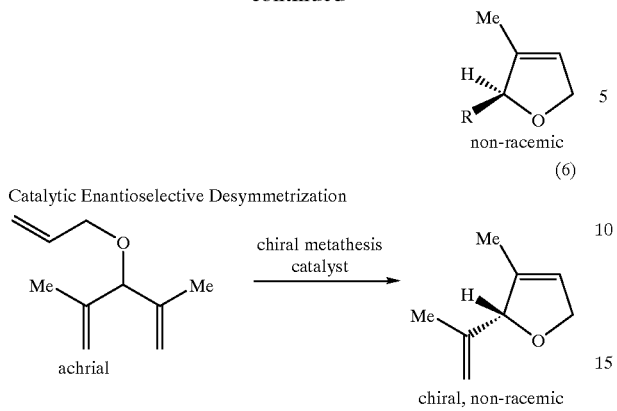

The desymmetrization reaction can be initiated by the addition of a catalyst, resulting in a catalytic desymmetrization reaction. In one embodiment, at a turnover number of at least about 5, at least one enantiomer of a product is formed in an enantiomeric excess of at least about 20%. "Turnover number" reflects catalyst efficiency and robustness. For example, sufficiently active catalysts can result in high reaction rates, which can translate into high turnover numbers. High turnover numbers are also achieved where catalysts are robust and sufficiently withstand decomposition. Consequently, robust catalysts can maintain the integrity of the catalyst structure and function over long periods of time. Preferably, the turnover number is at least about 10, more preferably at least about 25, more preferably still at least about 50 and more preferably still at least about 100. An advantageous feature of catalysts that produce high turnover numbers is that relatively low amounts of catalyst are required in the reaction mixture. Catalyst amounts are expressed in mol % relative to an amount of substrate. In a preferred embodiment, the catalyst can be present in an amount of less than about 15 mol %, preferably less than about 10 mol %, more preferably less than about 5 mol % and more preferably still less than about 1 mol %. Preferably, at least one enantiomer is formed in an enantiomeric excess of at least about 50%, preferably at least about 85%, more preferably at least about 90%, still more preferably at least about 95% and still more preferably at least about 99%. In another embodiment, two enantiomers are formed in an enantiomeric excess of at least about 50%, preferably at least about 85%, more preferably at least about 90%, still more preferably at least about 95% and still more preferably at least about 99%.

The catalyst can be a metal complex. In one embodiment, the metal complex is a transition metal complex including at least one metal-carbon double bond. In this embodiment, the metal-carbon double bond can initiate an olefin metathesis reaction with the substrate. In another embodiment, the metal complex is a transition metal dialkoxide complex. In yet another embodiment, the transition metal dialkoxide complex comprises the structure I, as discussed previously.

In another embodiment, the molecular substrate can be selected from the group consisting of achiral and meso substrates. An "achiral" molecule is superimposable on its mirror image. Although a "meso" substrate possesses at least two chiral centers, this substrate also has a plane of symmetry, rendering meso substrates optically inactive. Both the substrate and product can be either cyclic or acyclic.

In one embodiment, the molecular substrate comprises a structure:

VI

The substrate possesses a plane of symmetry, in accordance with the present invention. In VI, A, B, D, E and $R^1$–$R^3$ can be the same or different and each of A, B, D, E and $R^1$–$R^3$ is selected from the group consisting of hydrogen, hydroxy, $C_1$–$C_{20}$ alkyl, $C_1$–$C_{20}$ alkenyl, $C_1$–$C_{20}$ aryl and $C_1$–$C_{20}$ alkynyl. $C_1$–$C_{20}$ alkyl, $C_1$–$C_{20}$ alkenyl, $C_1$–$C_{20}$ aryl and $C_1$–$C_{20}$ alkynyl are hydrocarbons optionally interrupted by a functional group including at least one non-carbon element. A "functional group including at least one non-carbon element" can include any one of a main group element, transition metal, lanthanide, actinide, a main group element containing substituent, transition metal containing substituent, lanthanide containing substituent, or an actinide containing substituent. For example, the functional group including a non-carbon element can be a metal ion or a metal-containing substituent having a number of ligands, the number of ligands being dictated by the ligand-type, ligand charge and a charge on the metal. The functional group can also be any main group element or a main group element appended to a number of substituents, the number being dictated by the elemental charge, the substituent-type and the charge on the substituent. In another embodiment, the functional group including at least one non-carbon element is selected from the group consisting of O, S, Se, silane, silyl ether, carbonyl, carboxyl, carboxylate, ether, ester, anhydride, acyl, cyano, $NO_2$, alkyloxy, aryloxy, hydroxy, hydroxyalkyl, amino, alkylamino, arylamino, amido, thioalkyl, thioaryl, sulfonate, phosphate, phosphonate, phosphane and stannane. The functional group can be reactive or nonreactive.

The symbol "▮" denotes either a double bond or a triple bond. In VI, "1▮" and "2▮" can be the same or different and each of "1▮" and "2▮" can be either a double or a triple bond. The bonds denoted by the symbol "⁓" do not necessarily conform to the geometry shown in the above structure. a, b, d, and e can be the same or different and each of a, b, d and e is an integer equaling 0 to 1. For example in the above structure, when "1▮" is a triple bond, a and b are zero, and the bonds to substituents A and B are eliminated. In this situation, at least the first atom of $R^3$, both carbon atoms of the triple bond and the adjacent carbon (bound to $R^1$) are arranged in an essentially linear fashion, as required by the sp hybridization of the carbon atoms of "1▮". When "1▮" is a double bond, a and b are equal to 1, the carbon atoms of the double bond are $sp^2$ hybridized and the substituents around "1▮" have a geometry approximated as shown by the above structure.

Either of "1▮" and "2▮" are reactive sites. For example, either of "1▮" and "2▮" can be involved in an olefin metathesis reaction. Metathesis can occur between both "1▮" groups or between one "1▮" group and a "2▮" group. The method of the present invention provides metathesis reactions involving different combinations of double and triple bonded groups. For example, both "1▮" and "2▮" can be a double bond and a reaction involving one "1∎" group and "2∎" can result to form an alkene/alkene metathesis product; both "1∎" and "2∎" can be a triple bond and a reaction involving one "1∎" group and "2∎" can result to form an alkyne/alkyne metathesis product; or "1∎" can be a triple bond and "2∎" can be a double bond or vice versa and a reaction involving one "1∎" group and "2∎" can result to form an alkyne/alkene metathesis product. Similar alkene/alkene and alkyne/alkyne combination reactions can also occur between both "1∎" groups. A substrate possessing an alkyne unit also has the potential to participate in at least two ring-closing metathesis reactions. For example, when an alkyne is involved in a first metathesis reaction, an alkene results which may participate in a subsequent second metathesis reaction.

In a preferred embodiment, the molecular substrate is involved in a ring-closing metathesis reaction, causing the formation of a cyclic structure. In the above structure, m and n are integers which can be the same and each of m and n are integers preferably equaling 0–20. The indices m and n represent a number of —$CH_2$— linker units in the substrate. Controlling the value of m and n in the substrate can allow control of the ring size in the resulting product. In another embodiment, m and n equal 0–10. In one embodiment, the product includes at least one ring having a ring size of less than about 20 atoms and preferably the ring size is less than about 10 atoms.

A non-limiting example of a molecular substrate comprises a structure:

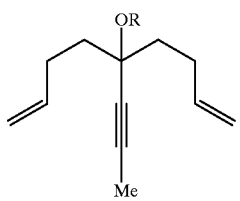

In this example, m=2, n=0, both "1∎" groups are double bonds and "2∎" is a triple bond. The catalyst can initiate a metathesis reaction with either the double bond or the triple bond of the substrate. In addition, there are two possible alignment orientations of the metal-carbon double bond of the catalyst with either a double or triple bond of the substrate immediately prior to metathesis. A resulting intermediate and the subsequent product can thus have various geometrical isomers. One example of a ring-closed product is shown in eq 7:

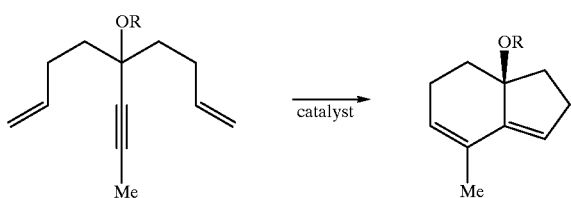

(7)

Equation 7 shows a bicyclic structure comprising fused closed-ring systems, specifically a fused five- and six-membered ring structure. The ring size can be varied by changing a number of —$CH_2$— of the substrate. One example of this variation in ring size is shown in eq 8 where m=3:

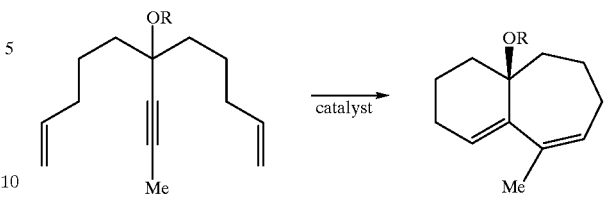

(8)

In this example, a fused six- and seven-membered ring structure is produced.

In another embodiment, the molecular substrate comprises a structure:

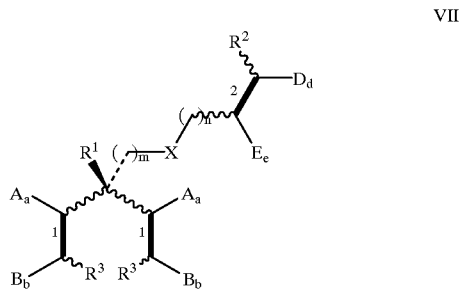

VII

In VII, "1∎" and "2∎" can be the same or different and each of "1∎" and "2∎" denotes a bond selected from the group consisting of a double bond and a triple bond. This structure includes "X", where X can be a functional substituent. A "functional substituent" as used herein can include any one of a main group element, transition metal, lanthanide, actinide, a main group element containing substituent, transition metal containing substituent, lanthanide containing substituent, an actinide containing substituent, or a saturated or unsaturated hydrocarbon $C_xH_y$ group, where x and y are at least 1. For example, the functional substituent can be a metal ion or a metal-containing substituent having a number of ligands, the number of ligands being dictated by the ligand-type, ligand charge and a charge on the metal. The functional substituent can also be any main group element or a main group element appended to a number of substituents, the number being dictated by the elemental charge, the substituent-type and the charge on the substituent. When "2∎" is involved in a ring-closing metathesis reaction, the product can include a heterocyclic ring. In one embodiment, X can be selected from the group consisting of $CR^8R^9$, carbonyl, ester, $SiR^8R^9$, $OSi(R^8)(R^9)$, $SnR^8R^9$, O, S, Se, $NR^8$, $PR^8$, and $PO_3R^8$. $R^8$ and $R^9$ can be the same or different and each of $R^8$ and $R^9$ is selected from the group consisting of hydrogen, $C_1$–$C_{20}$ alkyl, $C_1$–$C_{20}$ alkenyl, $C_1$–$C_{20}$ aryl and $C_1$–$C_{20}$ alkynyl.

In VII, A, B, D, E and $R^1$–$R^3$ can be the same or different and each of A, B, D, E and $R^1$–$R^3$ can be selected from the group consisting of hydrogen, hydroxy, $C_1$–$C_{20}$ alkyl, $C_1$–$C_{20}$ alkenyl, $C_1$–$C_{20}$ aryl and $C_1$–$C_{20}$ alkynyl. In all embodiments for VII, $C_1$–$C_{20}$ alkyl, $C_1$–$C_{20}$ alkenyl, $C_1$–$C_{20}$ aryl and $C_1$–$C_{20}$ alkynyl are hydrocarbons optionally interrupted by a functional group including at least one non-carbon element. In one embodiment, the functional group including at least one non-carbon element is selected from the group consisting of O, S, Se, silane, silyl ether, carbonyl, carboxyl, carboxylate, ether, ester, anhydride, acyl, cyano, $NO_2$, alkyloxy, aryloxy, hydroxy, hydroxyalkyl, amino, alkylamino, arylamino, amido, thioalkyl, thioaryl, sulfonate, phosphate, phosphonate, phosphane and stannane. In VII, a, b, d, and e can be the same or different and each of a, b, d and e is an integer equaling 0 to 1. m and n can be the same or different and each of m and n are integers preferably equaling 0–20, and more preferably equaling 0–10.

In another embodiment, the molecular substrate comprises a structure:

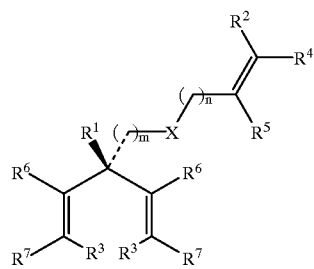

VIII

VIII is related to VII in that "1∎" and "2∎" of VII both represent double bonds and accordingly, a, b, d and e all equal 1. As discussed previously, any combination of double bonds can undergo an alkene/alkene metathesis reaction to form a cyclic structure. In a preferred embodiment, the product comprises a heterocycle including X. $R^1$–$R^3$, m and n are defined as in VII. In VIII, $R^4$–$R^7$ can be the same or different and each of $R^4$–$R^7$ is selected from the group consisting of hydrogen, hydroxy, $C_1$–$C_{20}$ alkyl, $C_1$–$C_{20}$ alkenyl, $C_1$–$C_{20}$ aryl and $C_1$–$C_{20}$ alkynyl.

Examples of enantioselective desymmetrization reactions are illustrated in eqs 9–11:

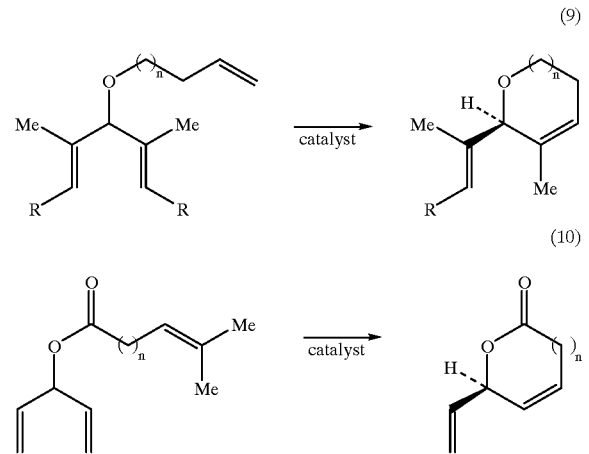

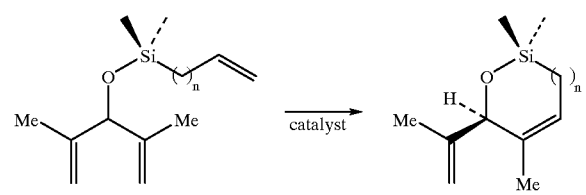

(11)

In another embodiment, the molecular substrate comprises a structure:

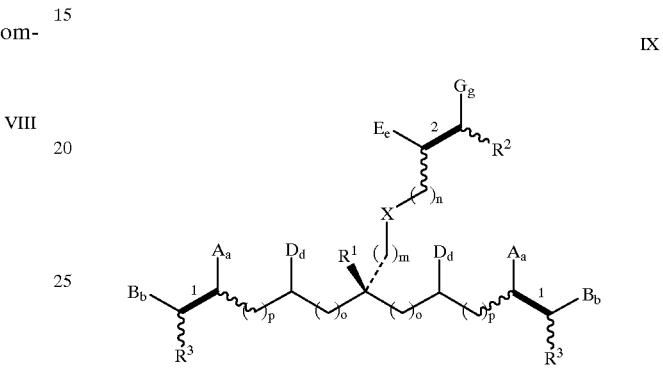

IX

When d=1 and D is a non-hydrogen element, IX represents a class of meso substrates. As discussed previously, although IX possesses two chiral centers, i.e. the carbon atoms bonded to $D_d$, the plane of symmetry renders this substrate optically inactive. IX can result in heterocyclic ring structures of various ring sizes.

In IX, "1∎" and "2∎" can be the same or different and each of "1∎" and "2∎" denotes a bond which can be selected from the group consisting of a double bond and a triple bond. As discussed previously, a metathesis reaction can occur between any combination of "1∎" and "2∎" along with double and triple bond combinations. a, b, d, e and g can be the same or different and each of a, b, d, e and g are integers equaling 0 to 1. m, n, o and p can be the same or different and each of m, n, o and p are integers preferably equaling 0–20, and more preferably equaling 0–10. A, B, D, E, G and $R^1$–$R^3$ can be the same or different and each of A, B, D, E, G and $R^1$–$R^3$ is selected from the group consisting of hydrogen, hydroxy, $C_1$–$C_{20}$ alkyl, $C_1$–$C_{20}$ alkenyl, $C_1$–$C_{20}$ aryl and $C_1$–$C_{20}$ alkynyl. X can be a functional substituent. In another embodiment, X can be selected from the group consisting of $CR^9R^{10}$, carbonyl, ester, $SiR^9R^{10}$, $OSi(R^9)(R^{10})$, $SnR^9R^{10}$, O, S, Se, $NR^9$, $PR^9$ and $PO_3R^9$. $R^9$ and $R^{10}$ can be selected from the group consisting of hydrogen, $C_1$–$C_{20}$ alkyl, $C_1$–$C_{20}$ alkenyl, $C_1$–$C_{20}$ aryl and $C_1$–$C_{20}$ alkynyl. In all embodiments of IX, $C_1$–$C_{20}$ alkyl, $C_1$–$C_{20}$ alkenyl, $C_1$–$C_{20}$ aryl and $C_1$–$C_{20}$ alkynyl are hydrocarbons optionally interrupted by a functional group including at least one non-carbon element. In one embodiments, the functional group including at least one non-carbon element can be selected from the group consisting of O, S, Se, silane, silyl ether, carbonyl, carboxyl, carboxylate, ether, ester, anhydride, acyl, cyano, $NO_2$, alkyloxy, aryloxy, hydroxy, hydroxyalkyl, amino, alkylamino, arylamino, amido, thioalkyl, thioaryl, sulfonate, phosphate, phosphonate, phosphane and stannane.

In another embodiment, the molecular substrate comprises a structure:

X

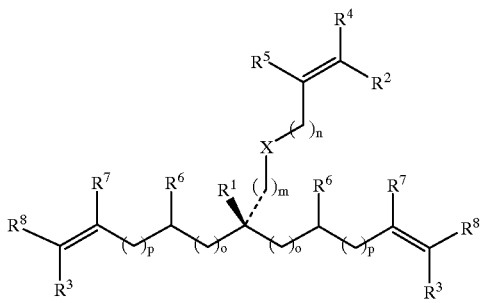

XI

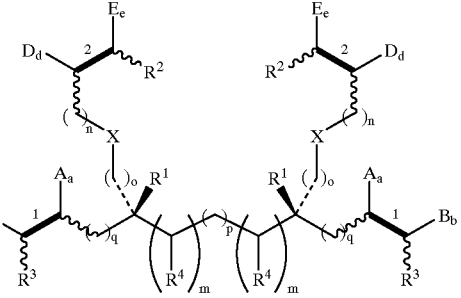

X is related to IX in that each of "1■" and "2■" represent double bonds and accordingly, each of a, b, d, e and g equal 1. $R^1$–$R^3$, X, m, n, o and p are as defined for IX. In X, $R^4$–$R^8$ can be the same or different and each of $R^4$–$R^8$ is selected from the group consisting of hydrogen, $C_1$–$C_{20}$ alkyl, $C_1$–$C_{20}$ alkenyl, $C_1$–$C_{20}$ aryl and $C_1$–$C_{20}$ alkynyl. $C_1$–$C_{20}$ alkyl, $C_1$–$C_{20}$ alkenyl, $C_1$–$C_{20}$ aryl and $C_1$–$C_{20}$ alkynyl are hydrocarbons optionally interrupted by a functional group including at least one non-carbon element.

Non-limiting examples of enantioselective metathesis reactions involving compounds in accordance with substrate X are illustrated in eqs 12 and 13:

(12)

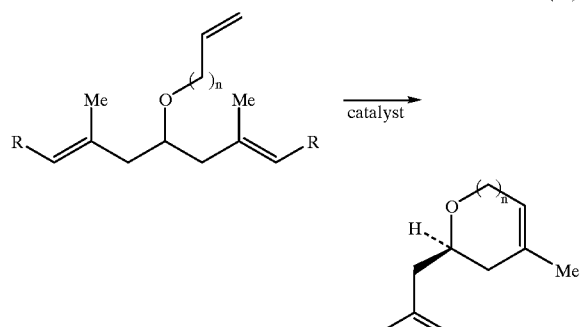

In another embodiment, the molecular substrate comprises a structure:

(13)

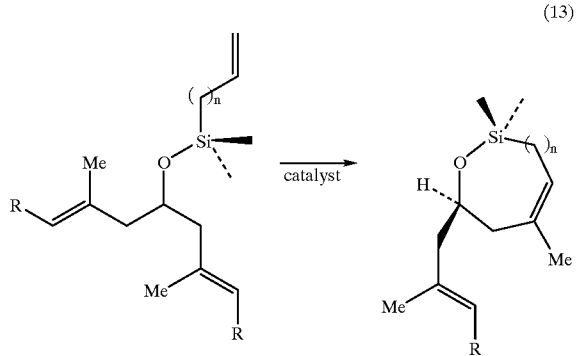

The substrate XI represents another class of meso substrates. In XI, "1■" and "2■" can be the same or different and each of "1■" and "2■" denotes a bond selected from the group consisting of a double bond and a triple bond. X can be a functional substituent. In another embodiment, X can be selected from the group consisting of $CR^9R^{10}$, carbonyl, ester, $SiR^9R^{10}$, $OSi(R^9)(R^{10})$, $SnR^9R^{10}$, O, S, Se, $NR^9$, $PR^9$ and $PO_3R^9$. $R^9$ and $R^{10}$ can be the same or different and each of $R^9$ and $R^{10}$ is selected from the group consisting of hydrogen, $C_1$–$C_{20}$ alkyl, $C_1$–$C_{20}$ alkenyl, $C_1$–$C_{20}$ aryl and $C_1$–$C_{20}$ alkynyl. a, b, d and e can be the same or different and each of a, b, d and e are integers equaling 0 to 1. m, n, o, p and q can be the same or different and each of m, n, o, p and q are integers preferably equaling 0–20, and more preferably equaling 0–10. A, B, D, E and $R^1$–$R^4$ can be the same or different and each of A, B, D, E and $R^1$–$R^4$ is selected from the group consisting of hydrogen, $C_1$–$C_{20}$ alkyl, $C_1$–$C_{20}$ alkenyl, $C_1$–$C_{20}$ aryl and $C_1$–$C_{20}$ alkynyl. In all embodiments for XI, $C_1$–$C_{20}$ alkyl, $C_1$–$C_{20}$ alkenyl, $C_1$–$C_{20}$ aryl and $C_1$–$C_{20}$ alkynyl are hydrocarbons optionally interrupted by a functional group including at least one non-carbon element. In one embodiment, the functional group including at least one non-carbon element is selected from the group consisting of O, S, Se, silane, silyl ether, carbonyl, carboxyl, carboxylate, ether, ester, anhydride, acyl, cyano, $NO_2$, alkyloxy, aryloxy, hydroxy, hydroxyalkyl, amino, alkylamino, arylamino, amido, thioalkyl, thioaryl, sulfonate, phosphate, phosphonate, phosphane and stannane.

In another embodiment, the molecular substrate comprises a structure:

XII

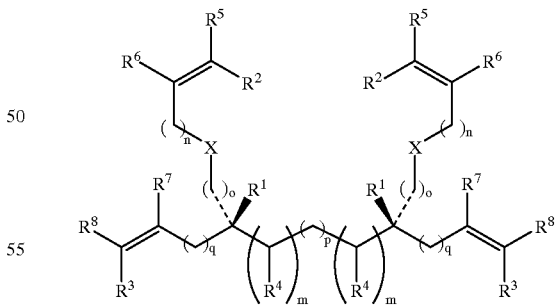

XII is related to XI, in that each of "1■" and "2■" represent double bonds and each of a, b, d and e equal 1. $R^1$–$R^4$, X, m, n, o, p and q are as defined for XI. In XII, $R^5$–$R^8$ can be the same or different and each of $R^5$–$R^8$ is a selected from the group consisting of hydrogen, $C_1$–$C_{20}$ alkyl, $C_1$–$C_{20}$ alkenyl, $C_1$–$C_{20}$ aryl and $C_1$–$C_{20}$ alkynyl, wherein $C_1$–$C_{20}$ alkyl, $C_1$–$C_{20}$ alkenyl, $C_1$–$C_{20}$ aryl and $C_1$–$C_{20}$ alkynyl are hydrocarbons optionally interrupted a functional group including at least one non-carbon element.

Non-limiting examples of enantioselective metathesis reactions involving meso substrates are illustrated in eqs 14 and 15:

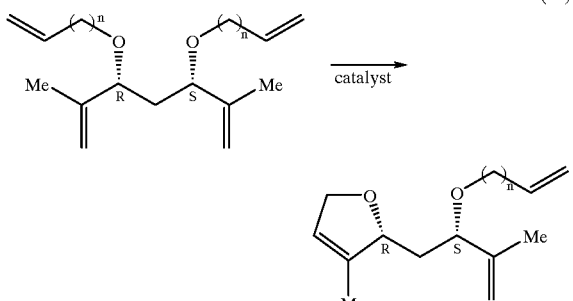

(14)

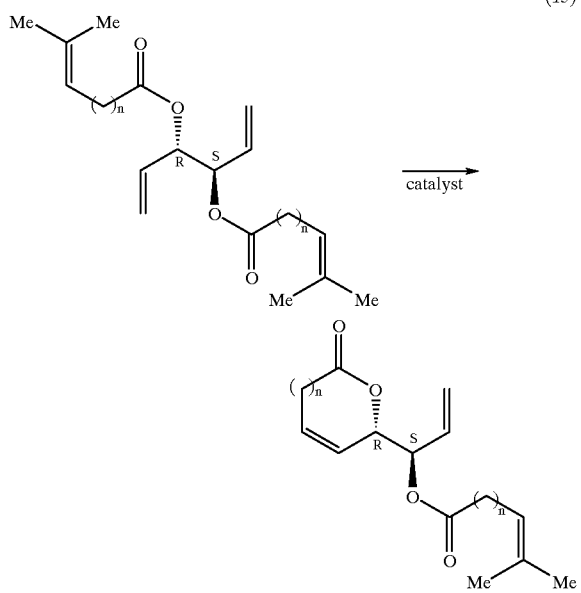

(15)

In another embodiment, the molecular substrate comprises a structure:

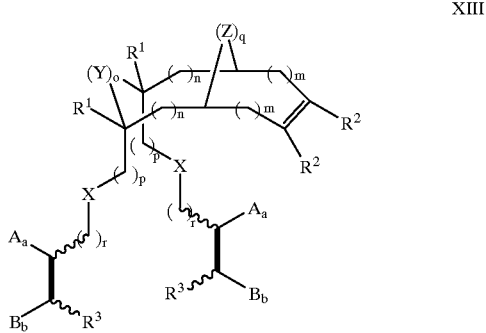

XIII

The substrate XIII can undergo a ring-opening metathesis reaction, where the catalyst initiates a metathesis reaction with the double bond of the substrate ring. XIII can also allow the formation of various fused-ring structures. "■" denotes a bond selected from the group consisting of a double bond and a triple bond. X, Y and Z can be the same or different and X, Y and X can be any functional substituent. In another embodiment, each of X, Y and Z is selected from the group consisting of $CR^6R^7$, carbonyl, ester, $SiR^6R^7$, $OSi(R^6)(R^7)$, $SnR^6R^7$, O, S, Se, $NR^6$, $PR^6$ and $PO_3R^6$. $R^6$ and $R^7$ can be the same or different and each of $R^6$ and $R^7$ is selected from the group consisting of hydrogen, $C_1$–$C_{20}$ alkyl, $C_1$–$C_{20}$ alkenyl, $C_1$–$C_{20}$ aryl and $C_1$–$C_{20}$ alkynyl. a and b can be the same or different and each of a and b are integers equaling 0 to 1. m, n, o, p, q and r can be the same or different and each of m, n, o, p, q and r are integers preferably equaling 0–20, and more preferably equaling 0–10, A, B and $R^1$–$R^3$ can be the same or different and each of A, B and $R^1$–$R^3$ is selected from the group consisting of hydrogen, $C_1$–$C_{20}$ alkyl, $C_1$–$C_{20}$ alkenyl, $C_1$–$C_{20}$ aryl and $C_1$–$C_{20}$ alkynyl. In all embodiments for XIII, $C_1$–$C_{20}$ alkyl, $C_1$–$C_{20}$ alkenyl, $C_1$–$C_{20}$ aryl and $C_1$–$C_{20}$ alkynyl are hydrocarbons optionally interrupted by a functional group including at least one non-carbon element. In one embodiment, the functional group including at least one non-carbon element is selected from the group consisting of O, S, Se, silane, silyl ether, carbonyl, carboxyl, carboxylate, ether, ester, anhydride, acyl, cyano, $NO_2$, alkyloxy, aryloxy, hydroxy, hydroxyalkyl, amino, alkylamino, arylamino, amido, thioalkyl, thioaryl, sulfonate, phosphate, phosphonate, phosphane and stannane.

In another embodiment, the molecular substrate comprises a structure:

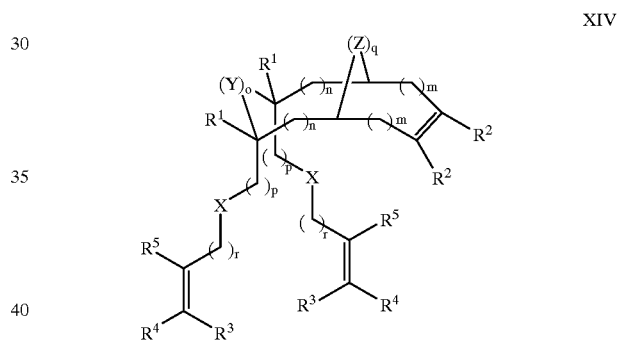

XIV

XIV is related to XIII in that "■" represents a double bond and accordingly, both a and b equal 1. $R^1$–$R^3$, X, Y, Z, m, n, o, p, q and r are as defined for XIII. In XIV, $R^4$ and $R^5$ can be the same or different and each of $R^4$ and $R^5$ is selected from the group consisting of hydrogen, $C_1$–$C_{20}$ alkyl, $C_1$–$C_{20}$ alkenyl, $C_1$–$C_{20}$ aryl and $C_1$–$C_{20}$ alkynyl. $C_1$–$C_{20}$ alkyl, $C_1$–$C_{20}$ alkenyl, $C_1$–$C_{20}$ aryl and $C_1$–$C_{20}$ alkynyl are hydrocarbons optionally interrupted by a functional group including at least one non-carbon element.

Non-limiting examples of ring-opening metathesis reactions are illustrated in eqs 16 and 17:

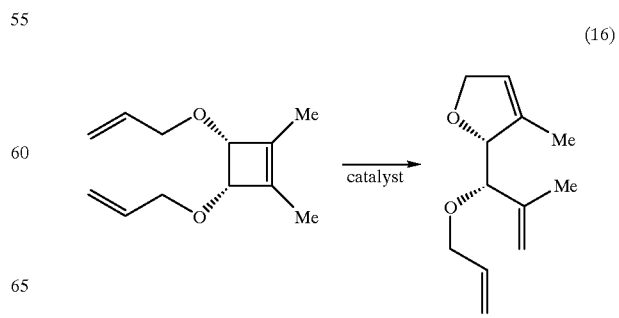

(16)

(17)

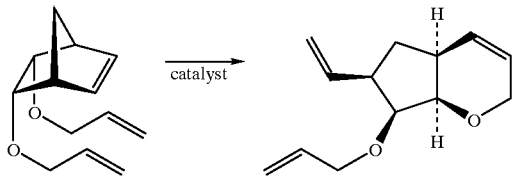

In another embodiment, the molecular substrate is a first molecular substrate and the method further comprises the addition of a second molecular substrate. The metathesis reaction can be a cross-metathesis reaction, allowing the formation of both cyclic and acyclic products. In this embodiment, the first molecular substrate can be selected from the group consisting of:

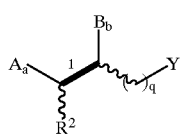 XV

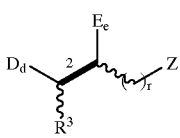 XVI and the second molecular substrate comprises a structure:

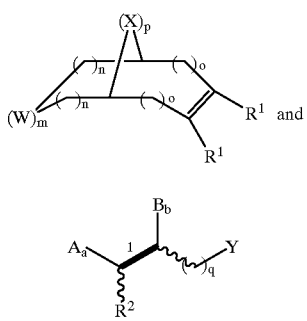 XVII

In XVI and XVII, "1■" and "2■" can be the same or different and each of "1■" and "2■" denotes a bond selected from the group consisting of a double bond and a triple bond. In XV, W and X can be the same or different and W and X can be any functional substituent. In another embodiment, each of W and X can be selected from the group consisting of $CR^8R^9$, carbonyl, ester, $SiR^8R^9$, $OSi(R^8)(R^9)$, $SnR^8R^9$, O, S, Se, $NR^8$, $PR^8$, $PO_3R^8$, $R^8$ and $R^9$ can be the same or different and each of $R^8$ and $R^9$ is selected from the group consisting of hydrogen, $C_1$–$C_{20}$ alkyl, $C_1$–$C_{20}$ alkenyl, $C_1$–$C_{20}$ aryl and $C_1$–$C_{20}$ alkynyl. a, b, d and e can be the same or different and each of a, b, d and e are integers equaling 0 to 1. m, n, o, p, q and r can be the same or different and each of m, n, o, p, q and r are integers preferably equaling 0–20, and more preferably equaling 0–10. A, B, D, E and $R^1$–$R^3$ can be the same or different and each of A, B, D, E and $R^1$–$R^3$ can be selected from the group consisting of hydrogen, $C_1$–$C_{20}$ alkyl, $C_1$–$C_{20}$ alkenyl, $C_1$–$C_{20}$ aryl and $C_1$–$C_{20}$ alkynyl. In XVI and XVII, Y and Z can be the same or different and each of Y and Z is selected from the group consisting of CN, carboxylic ester, amide, acid, halogen, hydrogen, $C_1$–$C_{20}$ alkyl, $C_1$–$C_{20}$ alkenyl, $C_1$–$C_{20}$ aryl and $C_1$–$C_{20}$ alkynyl. In all embodiments for XV–XVII, $C_1$–$C_{20}$ alkyl, $C_1$–$C_{20}$ alkenyl, $C_1$–$C_{20}$ aryl and $C_1$–$C_{20}$ alkynyl are hydrocarbons optionally interrupted a functional group including at least one non-carbon element. In one embodiment, the functional group including at least one non-carbon element selected from the group consisting of O, S, Se, silane, silyl ether, carbonyl, carboxyl, carboxylate, ether, ester, anhydride, acyl, cyano, $NO_2$, alkyloxy, aryloxy, hydroxy, hydroxyalkyl, amino, alkylamino, arylamino, amido, thioalkyl, thioaryl, sulfonate, phosphate, phosphonate, phosphane and stannane.

In another embodiment, the first molecular substrate can be selected from the group consisting of:

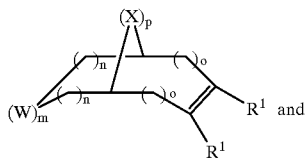 XV

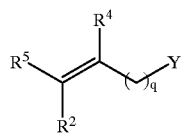 XVIII

Where the first molecular substrate comprise structure XV, a ring-opening metathesis reaction can occur. The second molecular substrate comprises a structure:

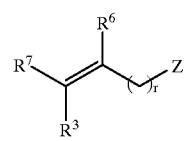 XIX

XVIII is related to XVI and XIX is related to XVII in that both "1■" and "2■" represent double bonds. $R^1$–$R^3$, W, X, Y, Z, m, n, o, p, q and r are as defined previously for XV–XVII. In XVIII and XIX, $R^4$–$R^7$ can be the same or different and each of $R^4$–$R^7$ is selected from the group consisting of hydrogen, $C_1$–$C_{20}$ alkyl, $C_1$–$C_{20}$ alkenyl, $C_1$–$C_{20}$ aryl and $C_1$–$C_{20}$ alkynyl, wherein $C_1$–$C_{20}$ alkyl, $C_1$–$C_{20}$ alkenyl, $C_1$–$C_{20}$ aryl and $C_1$–$C_{20}$ alkynyl are hydrocarbons optionally interrupted by a functional group including at least one non-carbon element.

Another aspect of the invention provides a method for catalytic desymmetrization in the absence of a solvent. A catalyst and a molecular substrate are provided, the substrate having a plane of symmetry. A desymmetrization reaction is allowed to occur in the absence of solvent to form a product free of a plane of symmetry. Performing catalytic reactions in the absence of solvents is an industrially advantageous feature. Elimination of highly volatile solvents can reduce the toxicity level. In addition, the expense of running the reaction is reduced. In one embodiment, the desymmetrization reaction can be a carbon-carbon bond formation reaction such as an olefin metathesis reaction and any previously discussed substrate can be used under solvent-free conditions.

Another aspect of the present invention provides a method for catalytic desymmetrization to form a quaternary carbon center. A quaternary carbon center is defined as a carbon atom bound to four non-hydrogen elements. In another embodiment, the four non-hydrogen elements can be carbon.

In a preferred embodiment, the quaternary carbon center is a chiral center. In general, quaternary carbon centers are difficult to form using conventional asymmetric synthesis techniques. Thus a feature of this aspect of the invention is the use of olefin metathesis to provide a general route to asymmetric quaternary carbon centers. A catalyst and a molecular substrate are provided, the molecular substrate having a plane of symmetry. A desymmetrization reaction is allowed to occur to form a product having a quaternary carbon center at a turnover number of at least about 5 in at least about 20% enantiomeric excess, preferably at least about a 50% enantiomeric excess, more preferably at least about an 85% enantiomeric excess, more preferably still at least about a 90% enantiomeric excess, more preferably still at least about a 95% enantiomeric excess and more preferably still at least about a 99% enantiomeric excess.

In one embodiment, the molecular substrate can comprise a structure selected from the group consisting of VI–XIV. Each of these structures can provide a quaternary carbon center when $R^1$ is a non-hydrogen element and the ring-closing olefin metathesis reaction does not solely involve two symmetric alkene or alkyne groups. Due to the plane of symmetry present in the substrate, the substrate is not optically active. Enantioselectivity is achieved upon ring formation. Examples of substrates in accordance with this aspect of the invention include:

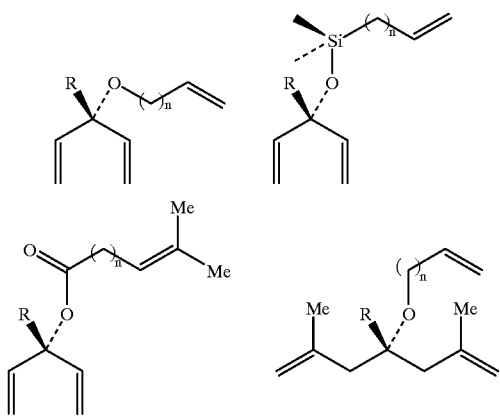

R is a non-hydrogen element. In addition, eqs 7 and 8 illustrate the formation of asymmetric quaternary carbon centers.

The function and advantage of these and other embodiments of the present invention will be more fully understood from the examples below. The following examples are intended to illustrate the benefits of the present invention, but do not exemplify the full scope of the invention.

EXAMPLE 1

Preparation and Resolution of t-Bu$_2$Me$_4$BiphenH$_2$

The compound t-Bu$_2$Me$_4$BiphenH$_2$ (1) was prepared from commercially available 3,4-

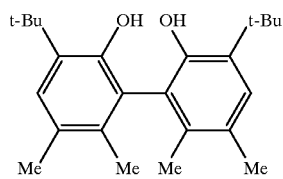

dimethylphenol in two steps. The phenol was alkylated at 65° C. under 2 atmospheres of isobutylene and a catalytic amount of suilfric acid. The crude trialkylphenol was oxidized directly to the biphenol with potassium chromate in hot acetic acid. The overall yield from 3,4-dimethyl phenol was ~50%.

The biphenol was resolved by selective crystallization using similar conditions to those reported by Wulff et al. to resolve a "vaulted" 2,2'-binaphthol and a vaulted 3,3'-biphenanthrol. The enantiomerically pure (−) biphenol was isolated employing (−) cinchonidine as the base. The specific rotation of the resolved biphenol was determined; [α]D=−53.0° (c=0.352, THF). All transition metal catalysts listed herein in the examples contain the (−) biphenol enantiomer.

EXAMPLE 2

Mo(N-2,6-i-Pr$_2$C$_6$H$_3$)(CHCMe$_2$Ph)[(−)-t-Bu$_2$Me$_4$Biphen] (2)

The compound (−) t-Bu$_2$Me$_4$BiphenH$_2$ (1) (500 mg, 1.16 mmol), was dissolved in THF (10 mL). Potassium hydride (2.1 eq, 98 mg) was added portionally as a solid. After 24 hours, additional THF (10 mL) was added and the suspension was filtered through celite. The THF solution was cooled to −30° C. Mo(NAr)(CHCMe$_2$Ph)(OTf)$_2$ (dimethoxyethane) (1.2 equiv, 1070 mg, 1.4 mmol) was dissolved in THF (15 mL) and the solution was cooled to −30° C. The THF solutions were combined and allowed to stir at room temperature for one hour and then stored overnight at −30° C. The volatiles were removed in vacuo and the red powder extracted with pentane. The slurry was filtered through celite to remove the potassium triflate. Removing the pentane yielded a spongy orange solid. Crystallization from concentrated diethyl ether gave 475 mg product in the first two crops (49%). $^1$H NMR (C$_6$D$_6$) δ 10.98 (s, 1H, =CHR), 7.42 (m, 3H, biph+Ph), 7.16 (m, 3H, biph+Ph), 7.05 (t, 1H, Ph), 6.92 (s, 3H, NAr), 3.70 (heptet, $J_{HH}$=7.0 Hz, 2H, CHMe$_2$), 2.132 (s, 3H), 2.147 (s, 3H), 1.850 (s, 3H), 1.739 (s, 3H), 1.662 (s, 3H) {2.13–1.66 ppm are 4 biphMe's and one CMe2Ph}, 1.595 (s, 9H, t-Bu), 1.542 (s, 9H, t-Bu), 1.145 (d, $J_{HH}$=7.0 Hz, 6H, CHMe$_2$), 1.133 (s, 3H, CMeMePh), 0.906 (d, $J_{HH}$=7.0 Hz, 6H, CHMe$_2$). $^{13}$C{$^1$H} NMR (C$_6$D$_6$) δ 277.07 (d, $J_{CH}$=123 Hz), 155.4, 154.5, 154.3, 151.3, 146.8, 140.0, 138.0, 136.5, 135.7, 132.0, 131.1, 130.9, 130.6, 129.6, 128.2, 127.9, 126.3, 123.8, 53.71, 35.95, 35.7, 34.7, 33.1, 33.0, 30.9, 30.4, 29.2, 24.6, 23.0, 20.8, 20.7, 17.2, 16.7, 14.6.

EXAMPLE 3

Mo(N-2.6-Me$_{2,6}$-Me$_2$C$_6$H$_3$)(CHCMe$_2$Ph)[(−)-t-Bu$_2$Me$_4$Biphen] (2')

This complex was prepared in the same method as for Mo(N-2,6-i-Pr$_2$C$_6$H$_3$)(CHCMe$_2$Ph)-[(−)-t-Bu$_2$Me$_4$Biphen] with one exception. Dissolving the pentane extract in benzene and then removing the solvent under vacuum gave a red sponge which became a powder after crushing. The purity of this compound was confirmed by $^1$H NMR. $^1$H NMR ($C_6D_6$)δ 11.01 (s, 1H, =CHR), 7.39 (s, 1H, biph), 7.25 (d, 2H, Ph), 7.11 (s, 1H, biph), 7.05 (t, 2H, Ph), 6.88 (t, 1H, Ph), 6.63 (s, 3H, NAr'), 2.218 (s, 6H, Ar'Me$_2$), 2.101 (s, 3H, biph), 1.968 (s, 3H, biph), 1.720 (s, 3H, biph), 1.608 (s, 3H, biph), 1.562 (s, 3H, CMe$_2$Ph), 1.532 (s, 9H, t-Bu), 1.505 (s, 9H, t-Bu), 1.200 (s, 3H, CMe$_2$Ph). $^{13}$C{$^1$H} NMR ($C_6D_6$) δ 278.94 (d, $J_{CH}$=120.6 Hz), 155.97, 155.10, 154.18, 150.94, 140.16, 138.28, 137.16, 136.82, 135.65, 132.10, 131.04, 130.91, 130.82, 130.47, 130.05, 128.51, 128.31, 127.38, 27.25, 236.35, 54.16, 36.00, 35.76, 32.83, 31.93, 30.92, 30.56, 20.84, 20.73, 19.80, 17.34, 16.82.

EXAMPLE 4

Conditions for the Kinetic Resolution of 4-triethylsilyloxide-5-methyl-1,6-octadiene (3)

Both 2 and 2' efficiently ring-close the substrate, 3-methyl-4-triethylsiloxide-2.7-diene (3), over several hours (eq 5). As an example, the optically active catalyst 2 (73 mg,

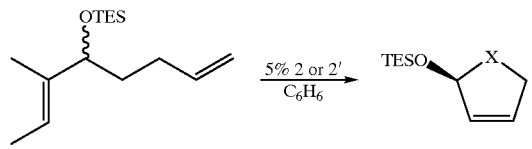

(18)

0.0984 mmol, 5%) was dissolved in toluene or benzene (20 mL). The substrate 3 was then added and the flask sealed with a plastic cap, After a period of time (1.5 or 23 hours), the reaction was opened to air and methanol added (1 mL). The volatile compounds were removed on a rotary evaporator and the resulting liquid was passed through an alumina plug with ether. The ether was removed affording a yellow liquid (470 mg, 95% mass conservation: assuming 50% conversion and all biphenH$_2$). The percent conversion was determined by integration of $^1$H NMR (500 MHz, CDCl$_3$) signals: starting material (3.9 ppm) and ring-closed product (average of 4.6 and 5.45 ppm). Full NMR data for 3 has been reported in the literature. The ring-closed product is separated from 3 and BiphenH$_2$ (1) by column chromatography on silica with 100% hexane gradually shifting to 10% CH$_2$Cl$_2$ in hexane. The diene and 1 (198 mg) and ring-closed product (170 mg) were collected separately. On standing overnight, 1 crystallized from resolved 3 and was recycled. The triethylsilyl group is removed by treatment with fluoride ion in wet tetrahydrofuran.

Figure 2:
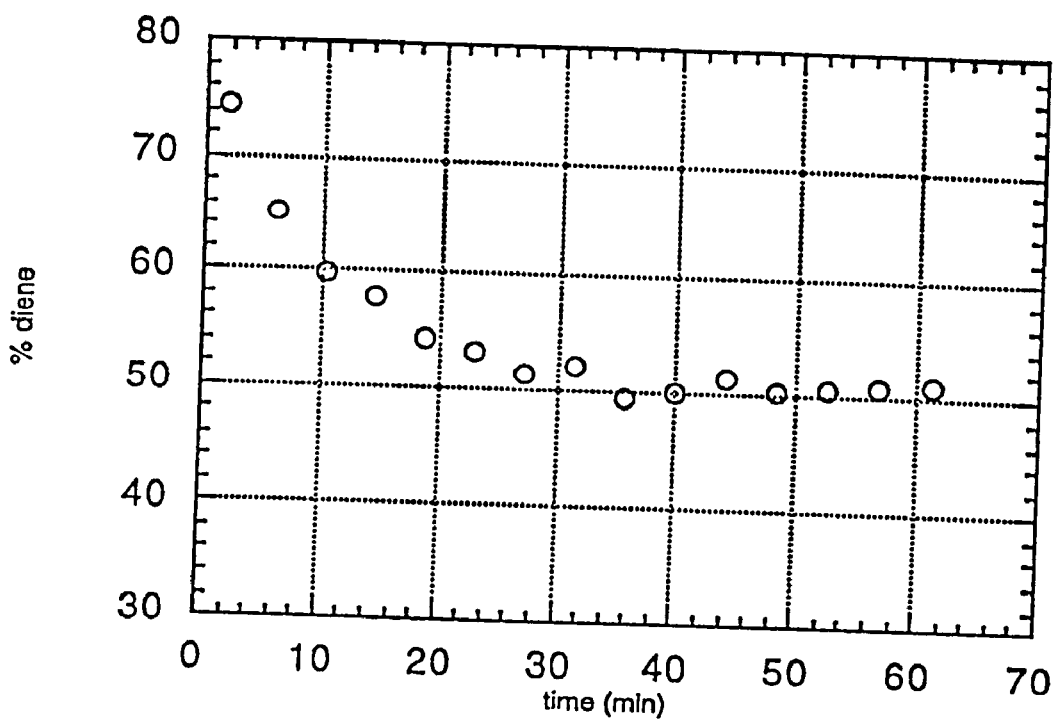
FIG. 2 shows a consumption plot in the reaction of the substrate 4-triethylsilyloxide-5-methyl-1,6-octadiene (3) with one enantiomer of $Mo(N-2,6-i-Pr_2C_6H_3)(CHCMe_2Ph)$ $[(-)-t-Bu_2Me_4Biphen]$ (2).

The consumption plot of 3, with 5% 2 obtained with the PAD(1) NMR macro (300 MHz), shows 50% conversion of starting material over 30 minutes and then no further significant conversion during the next half hour (FIG. 2). After 17 hours, the reaction is 57% complete. This indicates that the relative rate, S, is greater that 25.

Both diene and cyclopentene were then deprotected and derivatized. The diene (148 mg, 0.58 mmol) was added neat to a THF (5 mL) solution of [n-Bu$_4$NF]OH$_2$ (1.03 eq, 0.6 mmol, 167 mg). After stirring for 90 minutes at room temperature, the reaction was concentrated on a rotary evaporator and slurried in ether (10 mL). The solution was sequentially washed with water and brine and dried over MgSO$_4$. The purity of the isolated alcohol was confirmed by $^1$H NMR and compared favorably with the literature.

The free alcohols are purified and treated with Mosher's acid chloride in pyridine to form a mixture of diastereomeric esters. A fraction of isolated alcohol (17 mg, 0.122 mmol) was dissolved in dry pyridine (2 mL). Neat Mosher's acid chloride (1.3 eq, 40 mg, 0.158 mmol) was added the mixture was allowed to stand overnight. The reaction was added dropwise onto ice water and extracted with ether (2×10 mL). The ether extracts were washed with water (4×10 mL) and brine (2×10 mL) and then dried with MgSO$_4$. Enantiomeric excess was determined by examining the trisubstituted olefinic resonances (both diene and ring-closed product) by 500 MHz $^1$H NMR. For the diene these resonances appeared at 5.64 and 5.56 ppm. In the ring-closed product the olefinic resonances are observed at 5.70/5.67 and 3.57/3.56 ppm (OMe in R*). The kinetic resolution was quenched at 90 minutes and 23 hours. The percent conversion and determined % e.e. are tabulated in Table 1. With the two data points the S value for this system is approximately 25.

TABLE 1

| Kinetic resolution of 3 with 2 | | | |
| --- | --- | --- | --- |
| Time (h) | Conversion (%) | % e.e. diene | % e.e. RCM |
| 1.5 | 50.6 | 84.7 | 70.6 |
| 23 | 55.3 | 87.8 | 62.0 |

EXAMPLE 5

General Conditions for Desymmetrization Reactions

Infrared (IR) spectra were recorded on Perkin Elmer 781 and 1608 spectrophotometers, $v_{max}$ in cm$^{-1}$. Bands are characterized as broad (br), strong (s), medium (m), and weak (w). $^1$H NMR spectra were recorded on Varian GN-400 (400 MHz), Unity 300 (300 MHz), and Varian VXR 500 (500 MHz) spectrometers. Chemical shifts are reported in ppm from tetramethylsilane with the solvent resonance as the internal standard (CHCl$_3$: δ 7.26). Data are reported as follows: chemical shift, multiplicity (s=singlet, d=doublet, t=triplet, q=quartet, br=broad, m=multiplet), coupling constants (Hz), integration and assignment. $^{13}$C NMR spectra were recorded on Varian GN-400 (100 MHz), Unity 300 (75 MHz), and Varian VXR 500 (125 MHz) spectrometers with complete proton decoupling. Chemical shifts are reported in ppm from tetramethylsilane with the solvent as the internal reference (CDCl$_3$: δ 77.7 ppm). Enantiomer ratios were determined by chiral GLC analysis (Alltech Associates Chiraldex GTA column (30m×0.25 mm) or Betadex 120 column (30 m×0.25 mm) in comparison with authentic materials. Microanalyses were performed by Robertson Microlit Laboratories (Madison, N.J.) and Microlytics Analytical Laboratories (Deefield, Mass.). High resolution mass spectrometry was performed by the University of Illinois and Massachusetts Institute of Technology Mass Spectrometry Laboratories.

All reactions were conducted in oven (135° C.) and flame-dried glassware under an inert atmosphere of dry argon. Benzene and toluene were distilled from sodium metal/benzophenone ketyl, dichloromethane was distilled from calcium hydride. Mo(NAr)(CHCMe$_2$Ph)(OTf)$_2$.DME was synthesized according to the procedure outlined by Schrock et al. in *J. Am. Chem. Soc.*, 1990, 112, 3875–3886. Mo(N—(iso—Pr)$_2$C$_6$H$_3$)—(CHCMe$_2$Ph)((S)-(-)-tert-Bu$_2$Me$_4$(biphen)) was synthesized as outlined in Example 2.

EXAMPLE 6

Procedure for desymmetrization of trienes (6) and (8)

Structures of substrates and products can be found in Table 2. A 10 mL round bottom flask was charged with 3-allyl-(2,4-dimethyl-1,4-pentadienyl)ether (6) (1.22 g, 8.00 mmol) in a glove box under an atmosphere of argon. The solution was subsequently charged with 1 mol % of 2' (54.0 mg, 0.80 mmol). The solution became dark red as the catalyst dissolved with vigorous gas evolution. The flask was capped with a septum with an 18 gauge needle inserted to vent the reaction to the glove box atmosphere. After 13 h, the reaction vessel was removed from the glove box, the mixture was exposed to air and a short path distillation head was attached to the flask. The product was collected in 98.5% purity as a colorless liquid (850 mg, 86.0%) by distillation under nitrogen at 128° C. Trace impurities were removed by silica gel chromatography (99:1 pentanes:ether), however the isolated yield is reduced to 60–65% due to product volatility. Results are summarized in Table 2.

EXAMPLE 7

Determination of stereochemical identity of catalytic desymmetrization products

Figure 3:
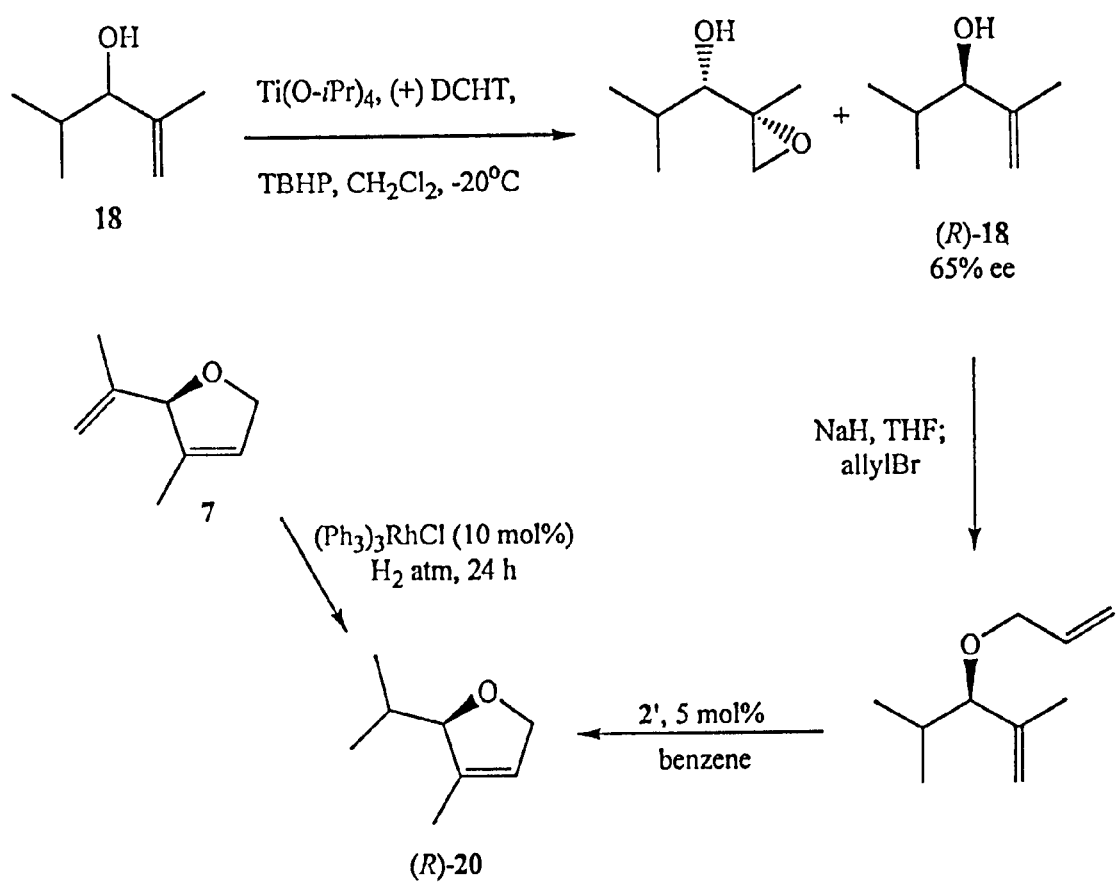
FIG. 3 shows a scheme for the determination of stereochemical identity of catalytic desymmetrization products, as outline in Example 7.

As illustrated in the scheme of FIG. 3, alcohol 18, obtained from the alkylation of isobutyraldehyde with 2-propenylmagnesiumbromide, was resolved by asymmetric epoxidation conditions of Sharpless to provide optically enriched alcohol (R)-18. Subsequent allylation, followed by catalytic RCM (5 mol %, (rac) 2') resulted in the formation of optically enhanced dihydrofuran (R)-20. The stereochemical configuration was equivalent to that of the catalytic hydrogenation of (7).

EXAMPLE 8

Representative procedure for Mo-catalyzed desymmetrization of quaternary center-containing trienes Triene 10 (32.4 mg, 0.123 mmol) was dissolved in anhydrous benzene (1.23 mL). The vessel was then charged with the optically active catalyst (−)-2 (4.29 mg, 0.00613 mmol, 5 mol %) and sealed with a teflon cap. After 24 h, the reaction was opened to air and MeOH was added (0.250 mL). The volatiles were removed on a rotary evaporator providing a dark brown residue. Purification by silica gel chromatography (500:1 hexane:Et$_2$O as the solvent) afforded 8.20 mg of 11 (0.0347 mmol, 28.2% yield) and 2.30 mg of substrate dimer. The

TABLE 2

Enantioselective Synthesis of Dihydrofurans by Mo-Catalyzed Desymmetrization.[a]

| entry | substrate | catalyst | temp (° C.), time | product | product ee (%), config.[b] | conv.,[c] yield (%)[d] |
|---|---|---|---|---|---|---|
| 1 | 6 | 2<br>2' | 22, 6 h<br>22, 6 h | | 93, R<br>93, R | 94, 82<br>93, 86 |
| 2 | 8 | 2<br>2' | 22, 9 h<br>22, 4 h | 9 | 94, R<br>99, R | 32, —<br>95, 83 |
| 3 | 10 | 2<br>2' | 22, 9 h<br>22, 4 h | 11 | —<br>50 | NO REACTION<br>42, 42 |
| 4 | 12 | 2<br>2' | 22, 15 h<br>22, 15 h | 13 | 10<br>10 | 76, 73<br>>98, 88 |

TABLE 2-continued

Enantioselective Synthesis of Dihydrofurans by Mo-Catalyzed Desymmetrization.[a]

| entry | substrate | catalyst | temp (° C.), time | product | product ee (%), config.[b] | conv.,[c] yield (%)[d] |
|---|---|---|---|---|---|---|
| 5 | 14 | 2<br>2' | 22, 18 h<br>−20, 18 h | 15 | 17, S<br>73, S | 87, 85<br>93, 84 |
| 6 | 16 | 2<br>2' | 22, 18 h<br>−20, 18 h | 17 | 16, S<br>82, S | 36, 34<br>93, 91 |

[a]Conditions: 5 mol % catalyst (1 mol %, entry 1), toluene for reactions at −25° C. and $C_6H_6$ for those at 22° C., Ar atm.
[b]Selectivity determined by chiral GLC (CHIRALDEX-GTA by Alltech for entries 1–4; BETADEX-120 by Alltech for entries 5–6) in comparison with authentic racemic material.
[c]Conversion determined by GLC analysis in comparison with dodecane as the internal standard (entries 1–2) or by $^1$H NMR analysis (400 MHz).
[d]Isolated yields after silica gel chromatography or distillation.

percent conversion was determined by $^1$H NMR (400 MHz) analysis of the unpurified mixture.

EXAMPLE 9

Procedural modifications for triene 12

The procedure for triene 12 was similar to that used for triene 10 with a few modifications. Triene 12 was dissolved in benzene (0.5 M), and the mixture (after addition of the catalyst), was allowed to stir for 15 h. The enantiomeric excess was determined by chiral GLC analysis of the derived alcohol (Betadex 120 column) obtained through 9BBN hydroboration of product 13.

EXAMPLE 10

Procedural modifications for trienes 14 and 16

The procedure used for ARCM of trienes 14 and 16 was similar to that employed for the reactions of triene 10 (see Example 8), but with a few modifications. Trienes 14 and 16 were dissolved in toluene to a concentration of 0.5 M and cooled to −20° C. the temperature was allowed to remain at −20° C. for the duration of the transformation.

Those skilled in the art would readily appreciate that all parameters listed herein are meant to be exemplary and that actual parameters will depend upon the specific application for which the methods and apparatus of the present invention are used. It is, therefore, to be understood that the foregoing embodiments are presented by way of example only and that, within the scope of the appended claims and equivalents thereto, the invention may be practiced otherwise than as specifically described.

What is claimed is:
1. A method for desymmetrization, comprising:
providing a catalyst and a molecular substrate having a plane of symmetry, the catalyst being present in an amount of less than 15 mol %, relative to an amount of substrate and comprising a formula:

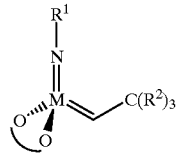

wherein the catalyst has a chiral dialkoxide ligand, denoted by

the dialkoxide being of at least 80% optical purity, M is a transition metal ion, and $R^1$ and each $R^2$ can be the same or different, and each is selected from the group consisting of $C_1$–$C_{12}$ alkyl, heteroalkyl, aryl, heteroaryl and adamantyl; and
causing an olefin metathesis reaction involving the molecular substrate to occur to form a product free of a plane of symmetry.
2. A method as in claim 1, wherein the molecular substrate is selected from the group consisting of achiral and meso substrates.
3. A method as in claim 1, wherein the molecular substrate is selected from the group consisting of cyclic and acyclic substrates.
4. A method as in claim 1, wherein the product is selected from the group consisting of cyclic and acyclic products.
5. A method as in claim 1, wherein the product includes at least one ring having a ring size of less than about 20 atoms.

6. A method as in claim 1, wherein the product includes at least one ring having a ring size of less than about 10 atoms.

7. A method as in claim 1, wherein the catalyst is present in an amount of less than about 10 mol %.

8. A method as in claim 1, wherein the catalyst is present in an amount of less than about 5 mol %.

9. A method as in claim 1, wherein the catalyst is present in an amount of less than about 1 mol %.

10. A method as in claim 1, wherein the molecular substrate comprises a structure:

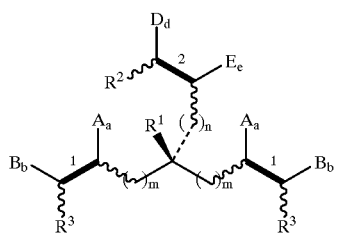

wherein "1▪" and "2▪" can be the same or different and each of "1▪" and "2▪" denotes a bond selected from the group consisting of a double bond and a triple bond; a, b, d, and e can be the same or different and each of a, b, d and e is an integer equaling 0 to 1; m and n can be the same or different and each of m and n are integers equaling 0–20; A, B, D, E and $R^1$–$R^3$ can be the same or different and each of A, B, D, E and $R^1$–$R^3$ is selected from the group consisting of hydrogen, hydroxy, $C_1$–$C_{20}$ alkyl, $C_1$–$C_{20}$ alkenyl, $C_1$–$C_{20}$ aryl and $C_1$–$C_{20}$ alkynyl, wherein $C_1$–$C_{20}$ alkyl, $C_1$–$C_{20}$ alkenyl, $C_1$–$C_{20}$ aryl and $C_1$–$C_{20}$ alkynyl are hydrocarbons optionally interrupted by a functional group including at least one non-carbon element.

11. A method as in claim 10, wherein each of m and n are integers equaling 0–10.

12. A method as in claim 10, wherein the functional group including at least one non-carbon element is selected from the group consisting of O, S, Se, silane, silyl ether, carbonyl, carboxyl, carboxylate, ether, ester, anhydride, acyl, cyano, $NO_2$, alkyloxy, aryloxy, hydroxy, hydroxyalkyl, amino, alkylamino, arylamino, amido, thioalkyl, thioaryl, sulfonate, phosphate, phosphonate, phosphane and stannane.

13. A method as in claim 1, wherein the molecular substrate comprises a structure:

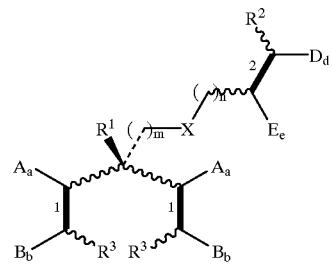

wherein "1▪" and "2▪" can be the same or different and each of "1▪" and "2▪" denotes a bond selected from the group consisting of a double bond and a triple bond; X is a functional substituent; a, b, d, and e can be the same or different and each of a, b, d and e is an integer equaling 0 to 1; m and n can be the same or different and each of m and n are integers equaling 0–20; A, B, D, E and $R^1$–$R^3$ can be the same or different and each of A, B, D, E and $R^1$–$R^3$ is selected from the group consisting of hydrogen, hydroxy, $C_1$–$C_{20}$ alkyl, $C_1$–$C_{20}$ alkenyl, $C_1$–$C_{20}$ aryl and $C_1$–$C_{20}$ alkynyl, wherein $C_1$–$C_{20}$ alkyl, $C_1$–$C20$ alkenyl, $C_1$–$C_{20}$ aryl and $C_1$–$C_{20}$ alkynyl are hydrocarbons optionally interrupted by a functional group including at least one non-carbon element.

14. A method as in claim 13, wherein each of m and n are integers equaling 0–10.

15. A method as in claim 13, wherein the functional group including at least one non-carbon element is selected from the group consisting of O, S, Se, silane, silyl ether, carbonyl, carboxyl, carboxylate, ether, ester, anhydride, acyl, cyano, $NO_2$, alkyloxy, aryloxy, hydroxy, hydroxyalkyl, amino, alkylamino, arylamino, amido, thioalkyl, thioaryl, sulfonate, phosphate, phosphonate, phosphane and stannane.

16. A method as in claim 13, wherein X is selected from the group consisting of $CR^8R^9$, carbonyl, ester, $SiR^8R^9$, $OSi(R^8)(R^9)$, $SnR^8R^9$, O, S, Se, $NR^8$, $PR^8$ and $PO_3R^8$; $R^8$ and $R^9$ can be the same or different and each of $R^8$ and $R^9$ is selected from the group consisting of hydrogen, $C_1$–$C_{20}$ alkyl, $C_1$–$C_{20}$ alkenyl, $C_1$–$C_{20}$ aryl and $C_1$–$C_{20}$ alkynyl, wherein $C_1$–$C_{20}$ alkyl, $C_1$–$C_{20}$ alkenyl, $C_1$–$C_{20}$ aryl and $C_1$–$C_{20}$ alkynyl are hydrocarbons optionally interrupted by a functional group including at least one non-carbon element.

17. A method as in claim 13, wherein the molecular substrate comprises a structure:

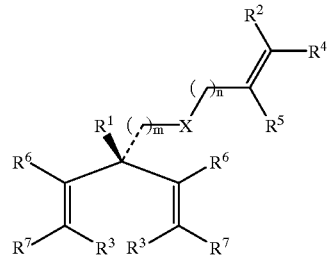

wherein $R^4$–$R^7$ can be the same or different and each of $R^4$–$R^7$ is selected from the group consisting of hydrogen, hydroxy, $C_1$–$C_{20}$ alkyl, $C_1$–$C_{20}$ alkenyl, $C_1$–$C_{20}$ aryl and $C_1$–$C_{20}$ alkynyl, wherein $C_1$–$C_{20}$ alkyl, $C_1$–$C_{20}$ alkenyl, $C_1$–$C_{20}$ aryl and $C_1$–$C_{20}$ alkynyl are hydrocarbons optionally interrupted by a functional group including at least one non-carbon element.

18. A method as in claim 17, wherein X is selected from the group consisting of $CR^8R^9$, carbonyl, ester, $SiR^8R^9$, $SiR^8R^9$, $OSi(R^8)(R^9)$, $SnR^8R^9$, O, S, Se, $NR^8$, $PR^8$, and $PO_3R^8$; $R^8$ and $R^9$ can be the same or different and each of $R^8$ and $R^9$ is selected from the group consisting of hydrogen, $C_1$–$C_{20}$ alkyl, $C_1$–$C_{20}$ alkenyl, $C_1$–$C_{20}$ aryl and $C_1$–$C_{20}$ alkynyl, wherein $C_1$–$C_{20}$ alkyl, $C_1$–$C_{20}$ alkenyl, $C_1$–$C_{20}$ aryl and $C_1$–$C_{20}$ alkynyl are hydrocarbons optionally interrupted by a functional group including at least one non-carbon element.

19. A method as in claim 1, wherein the molecular substrate comprises a structure:

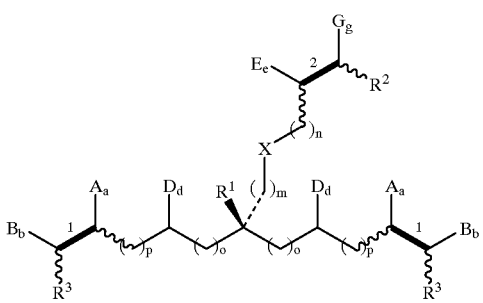

wherein "1∎" and "2∎" can be the same or different and each of "1∎" and "2∎" denotes a bond selected from the group consisting of a double bond and a triple bond; X is a functional substituent; a, b, d, e and g can be the same or different and each of a, b, d, e and g are integers equaling 0 to 1; m, n, o and p can be the same or different and each of m, n, o and p are integers equaling 0–20; A, B, D, E, G and $R^1$–$R^3$ can be the same or different and each of A, B, D, E, G and $R^1$–$R^3$ is selected from the group consisting of hydrogen, hydroxy, $C_1$–$C_{20}$ alkyl, $C_1$–$C_{20}$ alkenyl, $C_1$–$C_{20}$ aryl and $C_1$–$C_{20}$ alkynyl, and $C_1$–$C_{20}$ alkyl, $C_1$–$C_{20}$ alkenyl, $C_1$–$C_{20}$ aryl, wherein $C_1$–$C_{20}$ alkynyl are hydrocarbons optionally interrupted by a functional group including at least one non-carbon element.

20. A method as in claim 19, wherein each of m and n are integers equaling 0–10.

21. A method as in claim 19, wherein X is selected from the group consisting of $CR^9R^{10}$, carbonyl, ester, $SiR^9R^{10}$, $OSi(R^9)(R^{10})$, $SnR^9R^{10}$, O, S, Se, $NR^9$, $PR^9$ and $PO_3R^9$; $R^9$ and $R^{10}$ can be the same or different and each of $R^9$ and $R^{10}$ is selected from the group consisting of hydrogen, $C_1$–$C_{20}$ alkyl, $C_1$–$C_{20}$ alkenyl, $C_1$–$C_{20}$ aryl and $C_1$–$C_{20}$ alkynyl, wherein $C_1$–$C_{20}$ alkyl, $C_1$–$C_{20}$ alkenyl, $C_1$–$C_{20}$ aryl and $C_1$–$C_{20}$ alkynyl are hydrocarbons optionally interrupted by a functional group including at least one non-carbon element.

22. A method as in claim 19, wherein the molecular substrate comprises a structure:

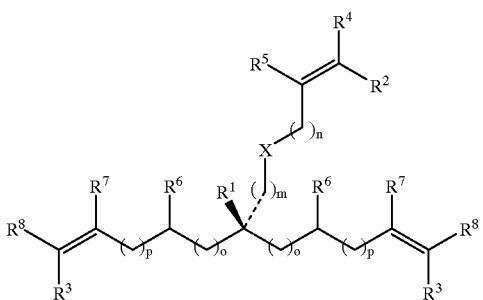

wherein $R^4$–$R^8$ can be the same or different and each of $R^4$–$R^8$ is selected from the group consisting of hydrogen, hydroxy, $C_1$–$C_{20}$ alkyl, $C_1$–$C_{20}$ alkenyl, $C_1$–$C_{20}$ aryl and $C_1$–$C_{20}$ alkynyl, wherein $C_1$–$C_{20}$ alkyl, $C_1$–$C_{20}$ alkenyl, $C_1$–$C_{20}$ aryl and $C_1$–$C_{20}$ alkynyl are hydrocarbons optionally interrupted by a functional group including at least one non-carbon element.

23. A method as in claim 22, wherein X is selected from the group consisting of $CR^9R^{10}$, carbonyl, ester, $SiR^9R^{10}$, $OSi(R^9)(R^{10})$, $SnR^9R^{10}$, O, S, Se, $NR^9$, $PR^9$ and $PO_3R^9$; $R^9$ and $R^{10}$ can be the same or different and each of $R^9$ and $R^{10}$ is selected from the group consisting of hydrogen, $C_1$–$C_{20}$ alkyl, $C_1$–$C_{20}$ alkenyl, $C_1$–$C_{20}$ aryl and $C_1$–$C_{20}$ alkynyl, wherein $C_1$–$C_{20}$ alkyl, $C_1$–$C_{20}$ alkenyl, $C_1$–$C_{20}$ aryl and $C_1$–$C_{20}$ alkynyl are hydrocarbons optionally interrupted by a functional group including at least one non-carbon element.

24. A method as in claim 1, wherein the molecular substrate comprises a structure:

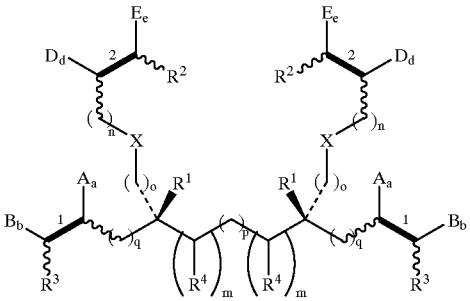

wherein "1∎" and "2∎" can be the same or different and each of "1∎" and "2∎" denotes a bond selected from the group consisting of a double bond and a triple bond; X is a functional substituent; a, b, d and e can be the same or different and each of a, b, d and e are integers equaling 0 to 1; m, n, o, p and q can be the same or different and each of m, n, o, p and q are integers equaling 0–20; A, B, D, E and $R^1$–$R^4$ can be the same or different and each of A, B, D, E and $R^1$–$R^4$ is selected from the group consisting of hydrogen, hydroxy, $C_1$–$C_{20}$ alkyl, $C_1$–$C_{20}$ alkenyl, $C_1$–$C_{20}$ aryl and $C_1$–$C_{20}$ alkynyl, wherein $C_1$–$C_{20}$ alkyl, $C_1$–$C_{20}$ alkenyl, $C_1$–$C_{20}$ aryl and $C_1$–$C_{20}$ alkynyl are hydrocarbons optionally interrupted by a functional group including at least one non-carbon element.

25. A method as in claim 24, wherein X is selected from the group consisting of $CR^9R^{10}$, carbonyl, ester, $SiR^9R^{10}$, $OSi(R^9)(R^{10})$, $SnR^9R$, O, S, Se, $NR^9$, $PR^9$ and $PO_3R^9$; $R^9$ and $R^{10}$ can be the same or different and each of $R^9$ and $R^{10}$ is selected from the group consisting of hydrogen, $C_1$–$C_{20}$ alkyl, $C_1$–$C_{20}$ alkenyl, $C_1$–$C_{20}$ aryl and $C_1$–$C_{20}$ alkynyl, wherein $C_1$–$C_{20}$ alkyl, $C_1$–$C_{20}$ alkenyl, $C_1$–$C_{20}$ aryl and $C_1$–$C_{20}$ alkynyl are hydrocarbons optionally interrupted by a functional group including at least one non-carbon element.

26. A method as in claim 24, wherein the molecular substrate comprises a structure:

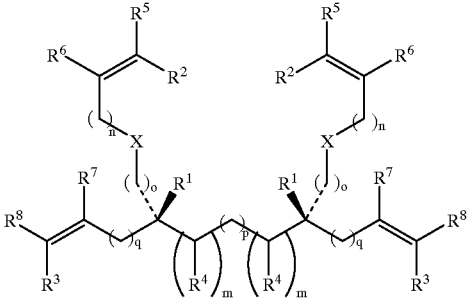

wherein $R^5$–$R^8$ can be the same or different and each of $R^5$–$R^8$ is a selected from the group consisting of hydrogen, hydroxy, $C_1$–$C_{20}$ alkyl, $C_1$–$C_{20}$ alkenyl, $C_1$–$C_{20}$ aryl and $C_1$–$C_{20}$ alkynyl, wherein $C_1$–$C_{20}$ alkyl, $C_1$–$C_{20}$ alkenyl, $C_1$–$C_{20}$ aryl, wherein $C_1$–$C_{20}$ alkynyl are hydrocarbons optionally interrupted a functional group including at least one non-carbon element.

27. A method as in claim 26, wherein X is selected from the group consisting of $CR^9R^{10}$, carbonyl, ester, $SiR^9R^{10}$, $OSi(R^9)(R^{10})$, $SnR^9R$, O, S, Se, $NR^9$, $PR^9$ and $PO_3R^9$; $R^9$ and $R^{10}$ can be the same or different and each of $R^9$ and $R^{10}$ is selected from the group consisting of hydrogen, $C_1$–$C_{20}$ alkyl, $C_1$–$C_{20}$ alkenyl, $C_1$–$C_{20}$ aryl and $C_1$–$C_{20}$ alkynyl, wherein $C_1$–$C_{20}$ alkyl, $C_1$–$C_{20}$ alkenyl, $C_1$–$C_{20}$ aryl and $C_1$–$C_{20}$ alkynyl are hydrocarbons optionally interrupted by a functional group including at least one non-carbon element.

28. A method as in claim 1, wherein the molecular substrate comprises a structure:

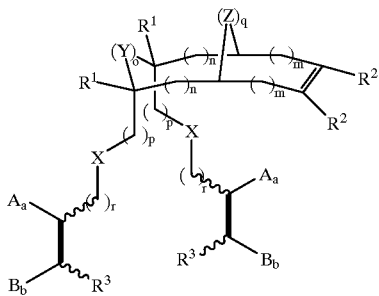

wherein "▋" denotes a bond selected from the group consisting of a double bond and a triple bond; X, Y and Z can be the same or different and X, Y and Z are functional substituents; a and b can be the same or different and each of a and b are integers equaling 0 to 1; m, n, o, p, q and r can be the same or different and each of m, n, o, p, q and r are integers equaling 0–20; A, B and $R^1$–$R^3$ can be the same or different and each of A, B and $R^1$–$R^3$ is selected from the group consisting of hydrogen, hydroxy, $C_1$–$C_{20}$ alkyl, $C_1$–$C_{20}$ alkenyl, $C_1$–$C_{20}$ aryl and $C_1$–$C_{20}$ alkynyl, wherein $C_1$–$C_{20}$ alkyl, $C_1$–$C_{20}$ alkenyl, $C_1$–$C_{20}$ aryl and $C_1$–$C_{20}$ alkynyl are hydrocarbons optionally interrupted by a functional group including at least one non-carbon element.

29. A method as in claim 30, wherein each of X, Y and Z is selected from the group consisting of $CR^6R^7$, carbonyl, ester, $SiR^6R^7$, $OSi(R^6)(R^7)$, $SnR^6R^7$, O, S, Se, $NR^6$, $PR^6$ and $PO_3R^6$; $R^6$ and $R^7$ can be the same or different and each of $R^6$ and $R^7$ is selected from the group consisting of hydrogen, $C_1$–$C_{20}$ alkyl, $C_1$–$C_{20}$ alkenyl, $C_1$–$C_{20}$ aryl and $C_1$–$C_{20}$ alkynyl, wherein $C_1$–$C_{20}$ alkyl, $C_1$–$C_{20}$ alkenyl, $C_1$–$C_{20}$ aryl and $C_1$–$C_{20}$ alkynyl are hydrocarbons optionally interrupted by a functional group including at least one non-carbon element.

30. A method as in claim 28, wherein the molecular substrate comprises a structure:

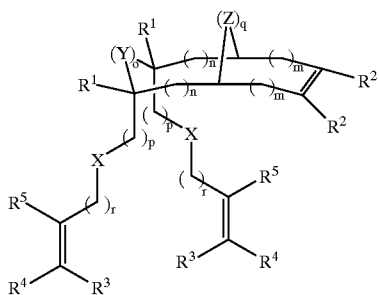

wherein $R^4$ and $R^5$ can be the same or different and each of $R^4$ and $R^5$ is selected from the group consisting of hydrogen, hydroxy, $C_1$–$C_{20}$ alkyl, $C_1$–$C_{20}$ alkenyl, $C_1$–$C_{20}$ aryl and $C_1$–$C_{20}$ alkynyl, wherein $C_1$–$C_{20}$ alkyl, $C_1$–$C_{20}$ alkenyl, $C_1$–$C_{20}$ aryl and $C_1$–$C_{20}$ alkynyl are hydrocarbons optionally interrupted by a functional group including at least one non-carbon element.

31. A method as in claim 30, wherein each of X, Y and Z is selected from the group consisting of $CR^6R^7$, carbonyl, ester, $SiR^6R^7$, $OSi(R^6)(R^7)$, $SnR^6R^7$, O, S, Se, $NR^6$, $PR^6$ and $PO_3R^6$; $R^6$ and $R^7$ can be the same or different and each of $R^6$ and $R^7$ is selected from the group consisting of hydrogen, $C_1$–$C_{20}$ alkyl, $C_1$–$C_{20}$ alkenyl, $C_1$–$C_{20}$ aryl and $C_1$–$C_{20}$ alkynyl, wherein $C_1$–$C_{20}$ alkyl, $C_1$–$C_{20}$ alkenyl, $C_1$–$C_{20}$ aryl and $C_1$–$C_{20}$ alkynyl are hydrocarbons optionally interrupted by a functional group including at least one non-carbon element.

32. A method as in claim 1, wherein the olefin metathesis reaction is selected from the group consisting of ring-closing metathesis and ring-opening metathesis.

33. A method as in claim 1, wherein the molecular substrate is a first molecular substrate, the method further comprising a second molecular substrate and the olefin metathesis reaction is a cross-metathesis reaction.

34. A method as in claim 33, wherein the first molecular substrate is selected from the group consisting of:

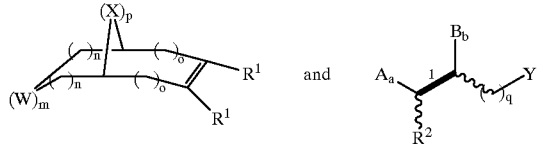

and the second molecular substrate comprises a structure:

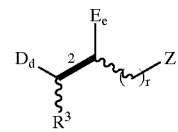

wherein "1▋" and "2▋" can be the same or different and each of "1▋" and "2▋" denotes a bond selected from the group consisting of a double bond and a triple bond; W and X can be the same or different and W and X are functional substituents; a, b, d and e can be the same or different and each of a, b, d and e are integers equaling 0 to 1; m, n, o, p, q and r can be the same or different and each of m, n, o, p, q and r are integers equaling 0–20; A, B, D, E and $R^1$–$R^3$ can be the same or different and each of A, B, D, E and $R^1$–$R^3$ is selected from the group consisting of hydrogen, hydroxy, $C_1$–$C_{20}$ alkyl, $C_1$–$C_{20}$ alkenyl, $C_1$–$C_{20}$ aryl and $C_1$–$C_{20}$ alkynyl, wherein $C_1$–$C_{20}$ alkyl, $C_1$–$C_{20}$ alkenyl, $C_1$–$C_{20}$ aryl and $C_1$–$C_{20}$ alkynyl are hydrocarbons optionally interrupted by a functional group including at least one non-carbon element; Y and Z can be the same or different and each of Y and Z is selected from the group consisting of CN, carboxylic ester, amide, acid, halogen, hydrogen, $C_1$–$C_{20}$ alkyl, $C_1$–$C_{20}$ alkenyl, $C_1$–$C_{20}$ aryl and $C_1$–$C_{20}$ alkynyl, wherein $C_1$–$C_{20}$ alkyl, $C_1$–$C_{20}$ alkenyl, $C_1$–$C_{20}$ aryl and $C_1$–$C_{20}$ alkynyl are hydrocarbons optionally interrupted a functional group including at least one non-carbon element.

35. A method as in claim 34, wherein each of W and X is selected from the group consisting of $CR^8R^9$, carbonyl, ester, $SiR^8R^9$, $OSi(R^8)(R^9)$, $SnR^8R^9$, O, S, Se, $NR^8$, $PR^8$ and $PO_3R^8$; $R^8$ and $R^9$ can be the same or different and each of $R^8$ and $R^9$ is selected from the group consisting of hydrogen, $C_1$–$C_{20}$ alkyl, $C_1$–$C_{20}$ alkenyl, $C_1$–$C_{20}$ aryl and $C_1$–$C_{20}$ alkynyl, wherein $C_1$–$C_{20}$ alkyl, $C_1$–$C_{20}$ alkenyl, $C_1$–$C_{20}$ aryl and $C_1$–$C_{20}$ alkynyl are hydrocarbons optionally interrupted by a functional group including at least one non-carbon element.

36. A method as in claim 34, wherein the first molecular substrate is selected from the group consisting of:

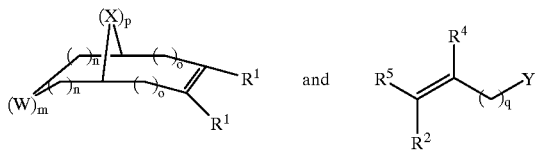

and the second molecular substrate comprises a structure:

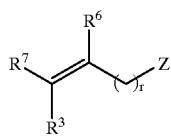

wherein $R^4$–$R^7$ can be the same or different and each of $R^4$–$R^7$ is selected from the group consisting of hydrogen, hydroxy, $C_1$–$C_{20}$ alkyl, $C_1$–$C_{20}$ alkenyl, $C_1$–$C_{20}$ aryl and $C_1$–$C_{20}$ alkynyl, wherein $C_1$–$C_{20}$ alkyl, $C_1$–$C_{20}$ alkenyl, $C_1$–$C_{20}$ aryl and $C_1$–$C_{20}$ alkynyl are hydrocarbons optionally interrupted by a functional group including at least one non-carbon element.

37. A method as in claim 36, wherein each of W and X is selected from the group consisting of $CR^8R^9$, carbonyl, ester, $SiR^8R^9$, $OSi(R^8)(R^9)$, $SnR^8R^9$, O, S, Se, $NR^8$, $PR^8$ and $PO_3R^8$; $R^8$ and $R^9$ can be the same or different and each of $R^8$ and $R^9$ is selected from the group consisting of hydrogen, $C_1$–$C_{20}$ alkyl, $C_1$–$C_{20}$ alkenyl, $C_1$–$C_{20}$ aryl and $C_1$–$C_{20}$ alkynyl, wherein $C_1$–$C_{20}$ alkyl, $C_1$–$C_{20}$ alkenyl, $C_1$–$C_{20}$ aryl and $C_1$–$C_{20}$ alkynyl are hydrocarbons optionally interrupted by a functional group including at least one non-carbon element.

38. A method as in claim 1, wherein the product is formed at a turnover number of at least about 5, the product being at least one enantiomer formed in an enantiomeric excess of at least about 20%.

39. A method as in claim 38, wherein the at least one enantiomer is formed in an enantiomeric excess of at least about 50%.

40. A method as in claim 38, wherein the at least one enantiomer is formed in an enantiomeric excess of at least about 85%.

41. A method as in claim 38, wherein the at least one enantiomer is formed in an enantiomeric excess of at least about 90%.

42. A method as in claim 38, wherein the at least one enantiomer is formed in an enantiomeric excess of at least about 95%.

43. A method as in claim 38, wherein the at least one enantiomer is formed in an enantiomeric excess of at least about 99%.

44. A method as in claim 38, wherein two enantiomers are each formed in an enantiomeric excess of at least about 20%.

45. A method as in claim 38, wherein the two enantiomers are each formed in an enantiomeric excess of at least about 50%.

46. A method as in claim 44, wherein the two enantiomers are each formed in an enantiomeric excess of at least about 85%.

47. A method as in claim 44, wherein the two enantiomers are each formed in an enantiomeric excess of at least about 90%.

48. A method as in claim 44, wherein the two enantiomers are each formed in an enantiomeric excess of at least about 95%.

49. A method as in claim 44, wherein the two enantiomers are each formed in an enantiomeric excess of at least about 99%.

50. A method as in claim 38, wherein the turnover number is at least about 10.

51. A method as in claim 38, wherein the turnover number is at least about 25.

52. A method as in claim 38, wherein the turnover number is at least about 50.

53. A method as in claim 38, wherein the turnover number is at least about 100.

54. A method as in claim 1, wherein $R^1$ is selected from the group consisting of 2,6-dimethylphenyl, 2,6-diethylphenyl and 2,6-diisopropylphenyl and $R^2$ is selected from the group consisting of methyl, ethyl and phenyl.

55. A method for desymmetrization, comprising:

providing a catalyst and a molecular substrate having a plane of symmetry, the catalyst being present in an amount of less than 15 mol %, relative to an amount of substrate and comprising a formula:

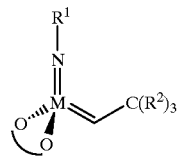

wherein the catalyst has a chiral dialkoxide ligand, denoted by

the dialkoxide being of at least 80% optical purity, M is a transition metal ion, and $R^1$ and each $R^2$ can be the same or different, and each is selected from the group consisting of $C_1$–$C_{12}$ alkyl, heteroalkyl, aryl, heteroaryl and adamantyl; and allowing a desymmetrization reaction to occur in the absence of solvent to form a product free of a plane of symmetry.

56. A method as in claim 55, wherein the desymmetrization is a catalytic desymmetrization and the providing step further comprises providing a catalyst.

57. A method as in claim 55, wherein the desymmetrization reaction is a carbon-carbon bond forming reaction.

58. A method as in claim 57, wherein the desymmetrization reaction is an olefin metathesis reaction.

59. A method as in claim 58, wherein the olefin metathesis reaction is selected from the group consisting of a ring-closing and a ring-opening reaction.

60. A method as in claim 58, wherein the molecular substrate is a first molecular substrate, the method further comprising a second molecular substrate and the olefin metathesis reaction is a cross-metathesis reaction.-

61. A method as in claim 56, wherein the desymmetrization reaction causes at least one enantiomer of a product to form in an enantiomeric excess of at least about 20% at a turnover number of at least about 5.

62. A method as in claim 61, wherein the at least one enantiomer is formed in an enantiomeric excess of at least about 50%.

63. A method as in claim 61, wherein the at least one enantiomer is formed in an enantiomeric excess of at least about 85%.

64. A method as in claim 61, wherein the at least one enantiomer is formed in an enantiomeric excess of at least about 90%.

65. A method as in claim 61, wherein the at least one enantiomer is formed in an enantiomeric excess of at least about 95%.

66. A method as in claim 61, wherein the at least one enantiomer is formed in an enantiomeric excess of at least about 99%.

67. A method as in claim 61, wherein two enantiomers are formed in an enantiomeric excess of at least about 20%.

68. A method for catalytic desymmetrization, comprising:

providing a molecular substrate having a plane of symmetry and a catalyst, the catalyst being present in an amount of less than 15 mol %, relative to an amount of substrate and comprising a formula:

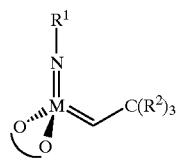

wherein the catalyst has a chiral dialkoxide ligand, denoted by

the dialkoxide being of at least 80% optical purity, M is a transition metal ion, and $R^1$ and each $R^2$ can be the same or different, and each is selected from the group consisting of $C_1$–$C_{12}$ alkyl, heteroalkyl, aryl, heteroaryl and adamantyl; and allowing a desymmetrization reaction to occur to form a product having a quaternary carbon center in at least about 20% enantiomeric excess.

69. A method as in claim 68, wherein the desymmetrization reaction is a carbon-carbon bond forming reaction.

70. A method as in claim 69, wherein the desymmetrization reaction is an olefin metathesis reaction.

* * * * *

UNITED STATES PATENT AND TRADEMARK OFFICE
CERTIFICATE OF CORRECTION

PATENT NO.      : 6,346,652 B1
DATED           : February 12, 2002
INVENTOR(S)     : Schrock et al.

It is certified that error appears in the above-identified patent and that said Letters Patent is hereby corrected as shown below:

Column 1,
Line 3, please replace "$SnR_9R$" with -- $SnR_9R_{10}$ --
Line 39, please replace "30" with -- 28 --

Column 2,
Line 3, replace "$C_1$-C20" with -- $C_1$-$C_{20}$ --.
Line 37, please replace "$SnR_9R$" with -- $SnR_9R_{10}$ --

Signed and Sealed this

Seventh Day of May, 2002

Attest:

JAMES E. ROGAN
*Attesting Officer*     *Director of the United States Patent and Trademark Office*

UNITED STATES PATENT AND TRADEMARK OFFICE
CERTIFICATE OF CORRECTION

PATENT NO.   : 6,346,652 B1
DATED        : February 12, 2002
INVENTOR(S)  : Schrock et al.

It is certified that error appears in the above-identified patent and that said Letters Patent is hereby corrected as shown below:

Column 34,
Line 3, please replace "$C_1$-C20" with -- $C_1$-$C_{20}$ --.

Column 36,
Line 37, please replace "$SnR^9R$" with -- $SnR^9R^{10}$ --.

Column 37,
Line 3, please replace "$SnR^9R$" with -- $SnR^9R^{10}$ --.
Line 39, please replace "30" with -- 28 --.

Signed and Sealed this

Twentieth Day of August, 2002

*Attest:*

*Attesting Officer*

JAMES E. ROGAN
*Director of the United States Patent and Trademark Office*